(12) United States Patent (10) Patent No.: US 8,891,084 B2
Durack (45) Date of Patent: Nov. 18, 2014

(54) MICROFLUIDIC DEVICE

(75) Inventor: Gary P. Durack, Urbana, IL (US)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 428 days.

(21) Appl. No.: 12/831,095

(22) Filed: Jul. 6, 2010

(65) Prior Publication Data

US 2011/0008767 A1 Jan. 13, 2011

Related U.S. Application Data

(60) Provisional application No. 61/224,533, filed on Jul. 10, 2009, provisional application No. 61/223,417, filed on Jul. 7, 2009, provisional application No. 61/223,408, filed on Jul. 7, 2009, provisional application No. 61/223,732, filed on Jul. 8, 2009, provisional application No. 61/223,735, filed on Jul. 8, 2009, provisional application No. 61/223,736, filed on Jul. 8, 2009, provisional application No. 61/223,737, filed on Jul. 8, 2009, provisional application No. 61/223,416, filed on Jul. 7, 2009, provisional application No. 61/223,419, filed on Jul. 7, 2009, provisional application No. 61/224,528, filed on Jul. 10, 2009, provisional application No. 61/223,420, filed on Jul. 7, 2009, provisional application No. 61/223,421, filed on Jul. 7, 2009, provisional application No. 61/223,406, filed on Jul. 7, 2009, provisional application No. 61/223,410, filed on Jul. 7, 2009, provisional application No. 61/223,407, filed on Jul. 7, 2009, provisional application No. 61/223,409, filed on Jul. 7, 2009, provisional application No. 61/223,734, filed on Jul. 8, 2009, provisional application No. 61/223,729, filed on Jul. 8, 2009.

(51) Int. Cl.
G01N 21/01 (2006.01)
G01N 33/36 (2006.01)
G01N 1/10 (2006.01)
B01L 3/00 (2006.01)
C12Q 1/02 (2006.01)

(52) U.S. Cl.
CPC ......... C12Q 1/025 (2013.01); B01L 2300/0877 (2013.01); B01L 2200/0647 (2013.01); B01L 3/5027 (2013.01); B01L 2300/0654 (2013.01)
USPC .......... 356/417; 356/244; 356/245; 356/246; 250/216; 250/573

(58) Field of Classification Search
CPC .......... B01L 3/5027; B01L 2200/0647; B01L 2300/0877; B01L 2300/0654; B01L 3/502776; B01L 15/1434; B01L 2400/084; B01L 2300/0816; C12Q 1/025; G01N 15/1404; G01N 29/222; G01N 21/645; G01N 21/64; G01N 15/147; G01N 21/1702; G01N 21/6428; G01N 2015/142; G01N 2291/02416; G01N 2291/02809; G01N 2291/02836; G01N 2015/1415
USPC .................................................. 356/244–246
See application file for complete search history.

(56) References Cited

U.S. PATENT DOCUMENTS

| | | |
|---|---|---|
| 3,526,219 A | 9/1970 | Balamuth |
| 3,814,098 A | 6/1974 | Deaton |
| 3,861,877 A | 1/1975 | Matharani et al. |
| 4,256,405 A | 3/1981 | Fjarlie |
| 4,465,488 A | 8/1984 | Richmond |
| 4,867,908 A | 9/1989 | Rechtenwald et al. |
| 4,988,619 A * | 1/1991 | Pinkel ............................ 435/30 |
| 5,157,465 A | 10/1992 | Kronberg |
| 5,315,122 A | 5/1994 | Pinsky et al. |
| 5,466,572 A | 11/1995 | Sasaki et al. |
| 5,478,722 A | 12/1995 | Caldwell |
| 5,726,751 A | 3/1998 | Altendorf et al. |
| 5,793,485 A | 8/1998 | Gourley |
| 6,100,541 A * | 8/2000 | Nagle et al. ................... 250/573 |
| 6,245,508 B1 | 6/2001 | Heller et al. |
| 6,268,219 B1 | 7/2001 | McBride et al. |
| 6,280,960 B1 | 8/2001 | Carr |
| 6,632,399 B1 | 10/2003 | Kellogg et al. |

| | | | |
|---|---|---|---|
| 6,877,528 B2 | 4/2005 | Gilbert et al. | |
| 6,900,021 B1 | 5/2005 | Harrison et al. | |
| 7,214,298 B2 | 5/2007 | Spence et al. | |
| 7,351,376 B1 | 4/2008 | Quake et al. | |
| 2002/0005354 A1 | 1/2002 | Spence et al. | |
| 2002/0127144 A1* | 9/2002 | Mehta | 422/81 |
| 2002/0173033 A1 | 11/2002 | Hammerick et al. | |
| 2003/0054558 A1 | 3/2003 | Kurabayashi et al. | |
| 2003/0199050 A1* | 10/2003 | Mangano et al. | 435/173.6 |
| 2004/0101439 A1* | 5/2004 | Fusco et al. | 422/57 |
| 2004/0219662 A1 | 11/2004 | Geiger | |
| 2004/0224380 A1 | 11/2004 | Chou et al. | |
| 2005/0006238 A1 | 1/2005 | Jaffe | |
| 2005/0009060 A1 | 1/2005 | Beernink et al. | |
| 2005/0105077 A1 | 5/2005 | Padmanabhan et al. | |
| 2005/0112541 A1 | 5/2005 | Durack et al. | |
| 2005/0260175 A1 | 11/2005 | Hedrick et al. | |
| 2006/0011478 A1 | 1/2006 | Fouillet et al. | |
| 2006/0024756 A1 | 2/2006 | Tibbe et al. | |
| 2006/0134003 A1 | 6/2006 | Georgakoudi et al. | |
| 2006/0194264 A1 | 8/2006 | Sheppard et al. | |
| 2006/0281143 A1 | 12/2006 | Liu et al. | |
| 2007/0095669 A1 | 5/2007 | Lau et al. | |
| 2007/0183934 A1 | 8/2007 | Diercks et al. | |
| 2007/0190525 A1 | 8/2007 | Gu et al. | |
| 2007/0215528 A1 | 9/2007 | Hayenga et al. | |
| 2007/0240495 A1 | 10/2007 | Hirahara | |
| 2007/0263477 A1 | 11/2007 | Sudarsan et al. | |
| 2008/0003690 A1 | 1/2008 | Chow | |
| 2008/0047836 A1 | 2/2008 | Strand et al. | |
| 2008/0072663 A1 | 3/2008 | Keenan et al. | |
| 2008/0107386 A1 | 5/2008 | Kudou et al. | |
| 2008/0176211 A1 | 7/2008 | Spence et al. | |
| 2008/0213915 A1 | 9/2008 | Durack et al. | |
| 2008/0300148 A1 | 12/2008 | Lee et al. | |
| 2009/0027666 A1 | 1/2009 | Godin et al. | |
| 2009/0051912 A1 | 2/2009 | Salazar et al. | |
| 2009/0053686 A1 | 2/2009 | Ward et al. | |
| 2009/0054529 A1 | 2/2009 | Neas et al. | |
| 2009/0081688 A1 | 3/2009 | Luo et al. | |
| 2009/0195852 A1 | 8/2009 | Bassler et al. | |
| 2009/0321398 A1* | 12/2009 | Mourou et al. | 219/121.69 |

FOREIGN PATENT DOCUMENTS

| | | |
|---|---|---|
| WO | WO 02/40978 A2 | 5/2002 |
| WO | WO 2008/019448 A1 | 2/2008 |

OTHER PUBLICATIONS

International Search Report and Written Opinion issued in PCT/US2010/040923, mailed Aug. 30, 2010.
International Search Report and Written Opinion Issued in PCT/US2010/041058, mailed Sep. 7, 2010.
International Search Report and Written Opinion issued in PCT/US2010/041062, mailed Aug. 20, 2010.
International Search Report and Written Opinion issued in PCT/US2010/041067, mailed Sep. 22, 2010.
International Search Report and Written Opinion issued in PCT/US2010/041094, mailed Sep. 2, 2010.
Nederlof et al. Multiple Fluorescence in situ hybridization; Cytometry, 1990, vol. 11, Iss. 1, pp. 126-131.
International Search Report and Written Opinion issued in PCT/US2010/041087, mailed Oct. 26, 2010.
International Search Report and Written Opinion Issued in PCT/US2010/041090, mailed Oct. 13, 2010.
Kang et al. Technical Paper on Microfluidic Devices Cell Separation Technology, Paper, Dec. 2005.
Tsutsui et al. Cell Separation by Non-Inertial Force Fields in Microfluidic Systems; Manuscript, Jan. 1, 2009.

* cited by examiner

*Primary Examiner* — Tarifur Chowdhury
*Assistant Examiner* — Sunghee Y Gray
(74) *Attorney, Agent, or Firm* — Ice Miller LLP

(57) ABSTRACT

The present disclosure relates to microfluidic devices adapted for facilitating cytometry analysis of particles flowing therethrough. In certain embodiments, the microfluidic devices allow light collection from multiple directions. In certain other embodiments, the microfluidic devices use spatial intensity modulation. In certain other embodiments, the microfluidic devices have magnetic field separators. In certain other embodiments, the microfluidic devices have the ability to stack. In certain other embodiments, the microfluidic devices have 3-D hydrodynamic focusing to align sperm cells. In certain other embodiments, the microfluidic devices have acoustic energy couplers. In certain other embodiments, the microfluidic devices have phase variation producing lenses. In certain other embodiments, the microfluidic devices have transmissive and reflective lenses. In certain other embodiments, the microfluidic devices have integrally-formed optics. In certain other embodiments, the microfluidic devices have non-integral geographically selective reagent delivery structures. In certain other embodiments, the microfluidic devices have optical waveguides incorporated into their flow channels. In certain other embodiments, the microfluidic devices have optical waveguides with reflective surfaces incorporated into their flow channels. In certain other embodiments, the microfluidic devices have virus detecting and sorting capabilities. In certain other embodiments, the microfluidic devices display a color change to indicate use or a result.

3 Claims, 24 Drawing Sheets

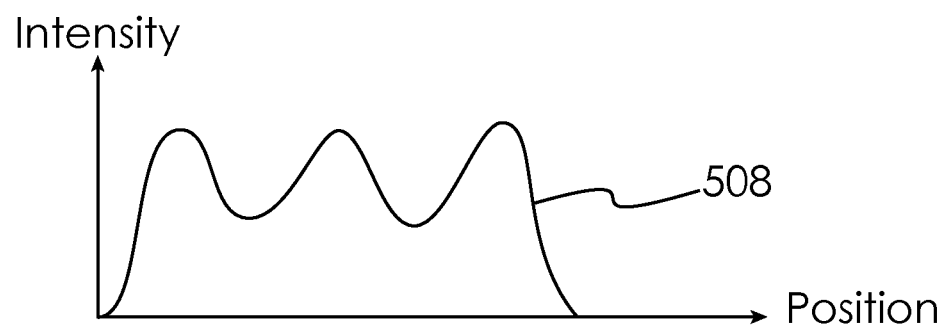
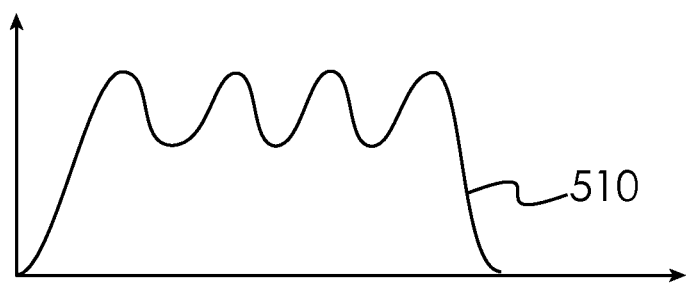
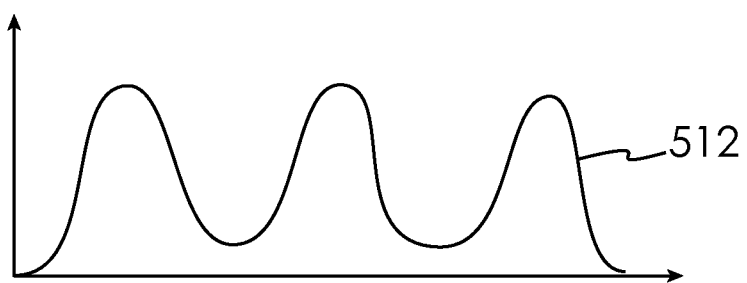
*Fig. 5*

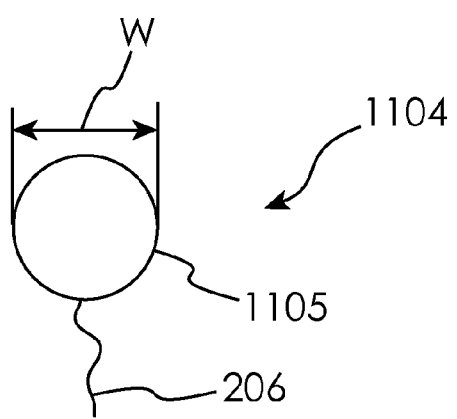 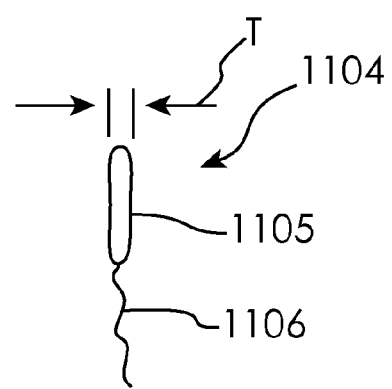
Fig. 12A  Fig. 12B

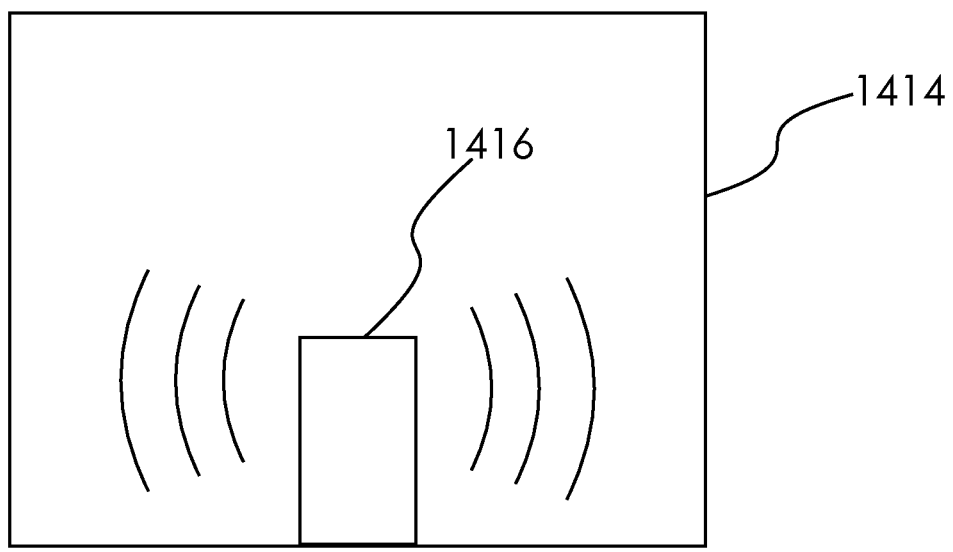
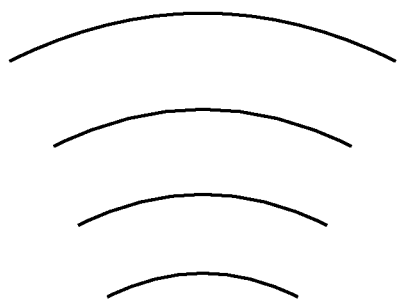
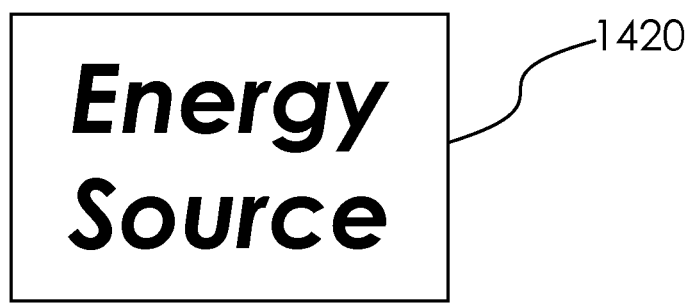
*Fig. 15*

MICROFLUIDIC DEVICE

CROSS-REFERENCE TO RELATED APPLICATIONS

The present application claims the benefit of the following: U.S. Provisional Patent Application No. 61/224,533, which was filed Jul. 10, 2009, U.S. Provisional Patent Application No. 61/223,417, which was filed Jul. 7, 2009, U.S. Provisional Patent Application No. 61/223,408, which was filed Jul. 7, 2009, U.S. Provisional Patent Application No. 61/223,732, which was filed Jul. 8, 2009, U.S. Provisional Patent Application No. 61/223,735, which was filed Jul. 8, 2009, U.S. Provisional Patent Application No. 61/223,736, which was filed Jul. 8, 2009, U.S. Provisional Patent Application No. 61/223,737, which was filed Jul. 8, 2009, U.S. Provisional Patent Application No. 61/223,416, which was filed Jul. 7, 2009, U.S. Provisional Patent Application No. 61/223,419, which was filed Jul. 7, 2009, U.S. Provisional Patent Application No. 61/224,528, which was filed Jul. 10, 2009, U.S. Provisional Patent Application No. 61/223,420, which was filed Jul. 7, 2009, U.S. Provisional Patent Application No. 61/223,421, which was filed Jul. 7, 2009, U.S. Provisional Patent Application No. 61/223,406, which was filed Jul. 7, 2009, U.S. Provisional Patent Application No. 61/223,410, which was filed Jul. 7, 2009, U.S. Provisional Patent Application No. 61/223,407, which was filed Jul. 7, 2009, U.S. Provisional Patent Application No. 61/223,409, which was filed Jul. 7, 2009, U.S. Provisional Patent Application No. 61/223,734, which was filed Jul. 8, 2009, and U.S. Provisional Patent Application No. 61/223,729, which was filed Jul. 8, 2009, all of which are hereby incorporated herein by reference in their entireties.

TECHNICAL FIELD OF THE DISCLOSURE

The present disclosure relates to microfluidic cytometry systems.

BACKGROUND OF THE DISCLOSURE

Flow cytometry-based cell sorting was first introduced to the research community more than 20 years ago. It is a technology that has been widely applied in many areas of life science research, serving as a critical tool for those working in fields such as genetics, immunology, molecular biology and environmental science. Unlike bulk cell separation techniques such as immuno-panning or magnetic column separation, flow cytometry-based cell sorting instruments measure, classify and then sort individual cells or particles serially at rates of several thousand cells per second or higher. This rapid "one-by-one" processing of single cells has made flow cytometry a unique and valuable tool for extracting highly pure sub-populations of cells from otherwise heterogeneous cell suspensions.

Cells targeted for sorting are usually labeled in some manner with a fluorescent material. The fluorescent probes bound to a cell emit fluorescent light as the cell passes through a tightly focused, high intensity, light beam (typically a laser beam). A computer records emission intensities for each cell. These data are then used to classify each cell for specific sorting operations. Flow cytometry-based cell sorting has been successfully applied to hundreds of cell types, cell constituents and microorganisms, as well as many types of inorganic particles of comparable size.

Flow cytometers are also applied widely for rapidly analyzing heterogeneous cell suspensions to identify constituent sub-populations. Examples of the many applications where flow cytometry cell sorting is finding use include isolation of rare populations of immune system cells for AIDS research, isolation of genetically atypical cells for cancer research, isolation of specific chromosomes for genetic studies, and isolation of various species of microorganisms for environmental studies. For example, fluorescently labeled monoclonal antibodies are often used as "markers" to identify immune cells such as T lymphocytes and B lymphocytes, clinical laboratories routinely use this technology to count the number of "CD4 positive" T cells in HIV infected patients, and they also use this technology to identify cells associated with a variety of leukemia and lymphoma cancers.

Recently, two areas of interest are moving cell sorting towards clinical, patient care applications, rather than strictly research applications. First is the move away from chemical pharmaceutical development to the development of biopharmaceuticals. For example, the majority of new cancer therapies are bio-based. These include a class of antibody-based cancer therapeutics. Cytometry-based cell sorters can play a vital role in the identification, development, purification and, ultimately, production of these products.

Related to this is a move toward the use of cell replacement therapy for patient care. Much of the current interest in stem cells revolves around a new area of medicine often referred to as regenerative therapy or regenerative medicine. These therapies may often require that large numbers of relatively rare cells be isolated from sample patient tissue. For example, adult stem cells may be isolated from bone marrow and ultimately used as part of a re-infusion back into the patient from whom they were removed. Cytometry lends itself very well to such therapies.

There are two basic types of cell sorters in wide use today. They are the "droplet cell sorter" and the "fluid switching cell sorter." The droplet cell sorter utilizes micro-droplets as containers to transport selected cells to a collection vessel. The micro-droplets are formed by coupling ultrasonic energy to a jetting stream. Droplets containing cells selected for sorting are then electrostatically steered to the desired location. This is a very efficient process, allowing as many as 90,000 cells per second to be sorted from a single stream, limited primarily by the frequency of droplet generation and the time required for illumination.

A detailed description of a prior art flow cytometry system is given in United States Published Patent Application No. US 2005/0112541 A1 to Durack et al.

Droplet cell sorters, however, are not particularly biosafe. Aerosols generated as part of the droplet formation process can carry biohazardous materials. Because of this, biosafe droplet cell sorters have been developed that are contained within a biosafety cabinet so that they may operate within an essentially closed environment. Unfortunately, this type of system does not lend itself to the sterility and operator protection required for routine sorting of patient samples in a clinical environment.

The second type of flow cytometry-based cell sorter is the fluid switching cell sorter. Most fluid switching cell sorters utilize a piezoelectric device to drive a mechanical system which diverts a segment of the flowing sample stream into a collection vessel. Compared to droplet cell sorters, fluid switching cell sorters have a lower maximum cell sorting rate due to the cycle time of the mechanical system used to divert the sample stream. This cycle time, the time between initial sample diversion and when stable non-sorted flow is restored, is typically significantly greater than the period of a droplet generator on a droplet cell sorter. This longer cycle time limits fluid switching cell sorters to processing rates of several hundred cells per second. For the same reason, the stream segment switched by a fluid cell sorter is usually at least ten times the volume of a single micro-drop from a droplet generator. This results in a correspondingly lower concentration of cells in the fluid switching sorter's collection vessel as compared to a droplet sorter's collection vessel.

Newer generation microfluidics technologies offer great promise for improving the efficiency of fluid switching devices and providing cell sorting capability on a chip similar in concept to an electronic integrated circuit. Many microfluidic systems have been demonstrated that can successfully sort cells from heterogeneous cell populations. They have the advantages of being completely self-contained, easy to sterilize, and can be manufactured on sufficient scales (with the resulting manufacturing efficiencies) to be considered a disposable part.

A generic microfluidic device is schematically illustrated in FIG. 1 and indicated generally at 10. The microfluidic device 10 comprises a substrate 12 having a fluid flow channel 14 formed therein by any convenient process as is known in the art. The substrate 12 may be formed from glass, plastic or any other convenient material, and may be substantially transparent or substantially transparent in a portion thereof. The substrate 12 further has three ports 16, 18 and 20 coupled thereto. Port 16 is an inlet port for a sheath fluid. Port 16 has a central axial passage that is in fluid communication with a fluid flow channel 22 that joins fluid flow channel 14 such that sheath fluid entering port 16 from an external supply (not shown) will enter fluid flow channel 22 and then flow into fluid flow channel 14. The sheath fluid supply may be attached to the port 16 by any convenient coupling mechanism as is known to those skilled in the art.

Port 18 also has a central axial passage that is in fluid communication with a fluid flow channel 14 through a sample injection tube 24. Sample injection tube 24 is positioned to be coaxial with the longitudinal axis of the fluid flow channel 14. Injection of a liquid sample of cells into port 18 while sheath fluid is being injected into port 16 will therefore result in the cells flowing through fluid flow channel 14 surrounded by the sheath fluid. The dimensions and configuration of the fluid flow channels 14 and 22, as well as the sample injection tube 24 are chosen so that the sheath/sample fluid will exhibit laminar flow as it travels through the device 10, as is known in the art. Port 20 is coupled to the terminal end of the fluid flow channel 14 so that the sheath/sample fluid may be removed from the microfluidic device 10.

While the sheath/sample fluid is flowing through the fluid flow channel 14, it may be analyzed using cytometry techniques by shining an illumination source through the substrate 12 and into the fluid flow channel 14 at some point between the sample injection tube 24 and the outlet port 20. Additionally, the microfluidic device 10 could be modified to provide for a cell sorting operation, as is known in the art.

Although basic microfluidic devices similar to that described hereinabove have been demonstrated to work well, there is a need in the prior art for improvements to cytometry systems employing microfluidic devices. The present invention is directed to meeting this need.

SUMMARY OF THE DISCLOSURE

The present disclosure relates to microfluidic devices adapted for facilitating cytometry analysis of particles flowing therethrough. In certain embodiments, the microfluidic devices allow light collection from multiple directions. In certain other embodiments, the microfluidic devices use spatial intensity modulation. In certain other embodiments, the microfluidic devices have magnetic field separators. In certain other embodiments, the microfluidic devices have the ability to stack. In certain other embodiments, the microfluidic devices have 3-D hydrodynamic focusing to align sperm cells. In certain other embodiments, the microfluidic devices have acoustic energy couplers. In certain other embodiments, the microfluidic devices have phase variation producing lenses. In certain other embodiments, the microfluidic devices have transmissive and reflective lenses. In certain other embodiments, the microfluidic devices have integrally-formed optics. In certain other embodiments, the microfluidic devices have non-integral geographically selective reagent delivery structures. In certain other embodiments, the microfluidic devices have optical waveguides incorporated into their flow channels. In certain other embodiments, the microfluidic devices have optical waveguides with reflective surfaces incorporated into their flow channels. In certain other embodiments, the microfluidic devices have virus detecting and sorting capabilities. In certain other embodiments, the microfluidic devices display a color change to indicate use or a result.

In one embodiment, a microfluidic device system is disclosed, comprising a substrate, a microfluidic flow channel formed in said substrate, wherein said flow channel extends through a portion of said substrate adapted to facilitate cytometry analysis of cells flowing in said flow channel, a first light collection device operative to collect light emitted by said cells in a first direction, said first light collection device producing a first output, a second light collection device operative to collect light emitted by said cells in a second direction, said second light collection device producing a second output, and detection optics operative to receive said first and second outputs.

In another embodiment, a method of detecting particles in a sample is disclosed, the method comprising the steps of: a) providing a microfluidic device, said microfluidic device comprising a substrate and a microfluidic flow channel formed in said substrate, wherein said flow channel extends through a portion of said substrate adapted to facilitate cytometry analysis of cells flowing in said flow channel; b) capturing first light emitted from said cells in a first direction; c) capturing second light emitted from said cells in a second direction; d) combining said first light and said second light captured at steps (b) and (c); and e) performing cytometry analysis on said combined first and second light.

In another embodiment, a method of detecting particles in a sample is disclosed, the method comprising the steps of: a) providing a microfluidic device, said microfluidic device comprising a substrate, a first microfluidic flow channel formed in said substrate, wherein said first flow channel extends through a portion of said substrate adapted to facilitate cytometry analysis of first cells flowing in said first flow channel, and a second microfluidic flow channel formed in said substrate, wherein said second flow channel extends through a portion of said substrate adapted to facilitate cytometry analysis of second cells flowing in said second flow channel; b) producing an excitation beam aimed at said first and second flow channels; c) spatially varying said excitation beam in a first manner prior to said excitation beam reaching said first flow channel; and d) spatially varying said excitation beam in a second manner prior to said excitation beam reaching said second flow channel.

In yet another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, a sample reception well formed onboard said substrate, said sample reception well being fluidically coupled to said flow channel, and an electromagnet disposed onboard said substrate and operative when energized to produce a magnetic field within said sample reception well.

In still another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, and at least one leg positioned on a surface of said substrate, said at least one leg facilitating stacking said microfluidic device on another microfluidic device.

In another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, and at least one hydrodynamic alignment structure fluidically coupled to said flow channel, said at least one hydrodynamic alignment structure operative to orient said cells such that a majority of said cells are analyzed from their largest dimension.

In yet another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, a well disposed onboard said substrate, said well being fluidically coupled with said flow channel, and an acoustic energy coupler disposed within said well.

In still another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, and a lens formed onboard said substrate, said lens operative to spatially modify an intensity of light passing therethrough.

In another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, a first lens formed onboard said substrate, said first lens being disposed on a first side of said flow channel, and a second lens formed onboard said substrate, said second lens being disposed on a second side of said flow channel.

In yet another embodiment, a microfluidic device is disclosed, comprising a substrate having a first surface, a microfluidic flow channel formed in said substrate, wherein said flow channel extends through a portion of said substrate adapted to facilitate cytometry analysis of cells flowing in said flow channel, and a lens formed onboard said substrate at said first surface, said lens lying below said first surface.

In still another embodiment, a microfluidic device is disclosed, comprising a substrate having a first surface, a reagent receiving well formed onboard said substrate, a reagent structure having a reagent disposed thereon, wherein application of said reagent structure to said first surface causes said reagent to align with said reagent receiving well for transfer of reagent thereto, and a microfluidic flow channel formed in said substrate, wherein said flow channel is fluidically coupled to said reagent receiving well.

In yet another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, and an optical waveguide formed in said flow channel.

In another embodiment, a microfluidic device is disclosed, comprising a substrate, a microfluidic flow channel formed in said substrate, wherein said flow channel extends through a portion of said substrate adapted to facilitate cytometry analysis of cells flowing in said flow channel, an optical waveguide formed in said flow channel, and a reflective surface disposed within said flow channel.

In yet another embodiment, a method of determining a pharmacological efficacy is disclosed, the method comprising the steps of: a) providing a microfluidic device, said microfluidic device comprising a substrate, a microfluidic flow channel formed in said substrate, wherein said flow channel extends through a portion of said substrate adapted to facilitate cytometry analysis of viral particles flowing in said flow channel, and a well formed onboard said substrate; b) depositing a material into said well; c) flowing said viral particles into said well; d) reacting said viral particles with said material; and e) determining a pharmacological efficacy of said material based upon said reaction.

In still another embodiment, a method of detecting particles in a sample is disclosed, the method comprising the steps of: a) providing a microfluidic device, said microfluidic device comprising a substrate, a microfluidic flow channel formed in said substrate, wherein said flow channel extends through a portion of said substrate adapted to facilitate cytometry analysis of cells flowing in said flow channel, and a dye repository formed onboard said substrate; b) depositing a dye into said well; c) performing a cytometry analysis on said cells; and d) causing said dye to exit said dye repository and enter said flow channel after said cytometry analysis is complete.

Other embodiments are also disclosed.

BRIEF DESCRIPTION OF THE DRAWINGS

FIG. 5 illustrates sample resultant fluorescence signals from the patterns of FIG. 4

FIG. 12a is a schematic top view of an example sperm cell.

FIG. 12b is a schematic side view of an example sperm cell.

FIG. 15 is a schematic front view of a chamber of a microfluidic device having an acoustic energy coupler.

DESCRIPTION OF THE ILLUSTRATED EMBODIMENTS

Figure 1:
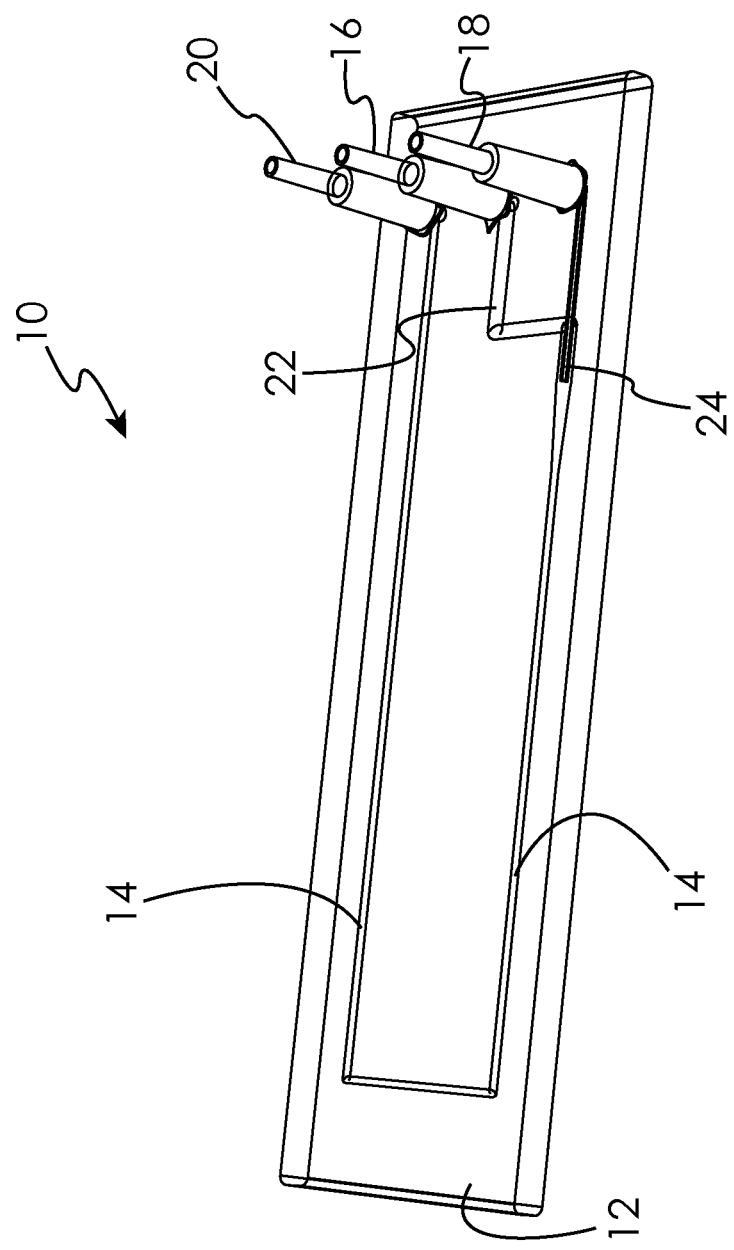
FIG. 1 is a perspective view of a prior art microfluidic device.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein are contemplated as would normally occur to one skilled in the art to which the disclosure relates.

Microfluidic Device Having Light Collection from Multiple Directions

Certain embodiments of the present disclosure are generally directed to systems for the analysis of a sample on a microfluidic device, using cytometry (such as flow cytometry or image cytometry). In order to detect or identify cells during cytometry operations, a source (such as a laser) of electromagnetic radiation (such as visible light) is directed to a detection area. When a cell passes through the detection area, the light source causes the cell to fluoresce. This effect may be enhanced by certain dyes which are added prior to the cell reaching the detection area. In most systems, the light source is applied to only one side of the cytometry device, with the detection optics also only detecting the fluorescence from one side of the sample cell. This limits the amount of photons that are captured from the fluorescent sample cell, since the photons emitted from other directions are not captured by the detection optics. The light intensity may be increased to generate more fluorescently generated photons, however this also increases the amount of noise in the signal.

In order to capture as many of the photons generated by a fluorescing sample cell as possible, light sources may be applied to multiple sides of the detection area. In addition, the detection optics can also be placed on multiple sides the detection area. This allows the system to capture more of the emitted photons for a given excitation light intensity without increasing the noise in the received signal. Further, the method combines the photons emitted from both sides into a single collimated path that can be focused on a single photodetector. This is an improvement over using separate photodetectors for each side. The use of two photodetectors doubles the noise contributed by each photodetector. Thus, the ability to use a single photodetector improves the signal-to-noise ratio of the system.

Figure 2:
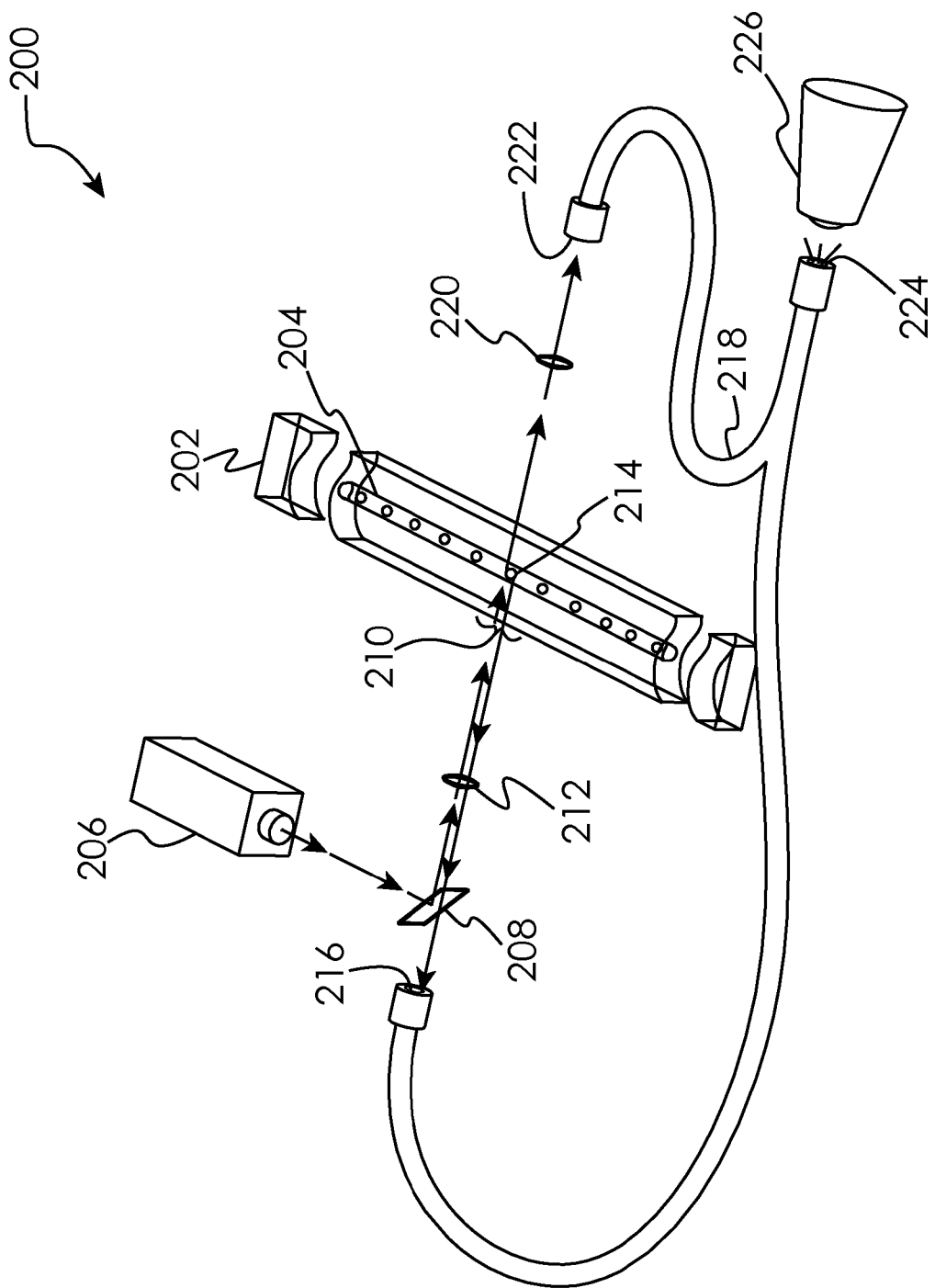
FIG. 2 is a schematic side view of a microfluidic device according to an embodiment of the present disclosure.

FIG. 2 schematically illustrates a system 200 for analyzing samples using cytometry. The system 200 may comprise a microfluidic device formed on substrate 202 (shown here from a side view) having a detection flow channel 204 contained therein. For simplicity and ease of illustration, FIG. 2 shows a single channel within the substrate 202. However, it should be appreciated that the single channel may be representative of multiple cytometry channels and a variety of possible configurations of channels as would occur to one skilled in the art. Various other cytometry components may also be contained on the cytometry chip 202 but are not critical to the present disclosure.

The system 200 may further comprise an excitation light source 206, a multi-core fiberoptic cable 218, focusing lenses 212 and 220, and detection optics 226. The lenses 212 and 220 may be placed outside of the substrate 202 as illustrated in FIG. 2, or may be mounted to or formed integrally within the substrate 202 depending the needs and cost considerations of the particular application. The excitation light source 206 may comprise a laser or other source of electromagnetic radiation known in the art. The detection optics 226 may comprise various light sensing means known in the art, such as photomultiplier tubes, photodiodes, or avalanche photodiodes.

In operation, excitation light source 206 (normally a laser) directs a light beam towards dichroic mirror 208. The dichroic mirror is configured to reflect the wavelength received from the light source 206 to the detection area 210 on the chip 202. Various other optical focusing components, such as lens 212, may be used to ensure proper focus of the excitation light source 206 onto the detection area 210. When a sample cell 214 traversing microfluidic flow channel 204 passes through the detection area 210 and fluoresces, the generated photons are emitted in many directions. Some photons will be emitted back toward the focusing lens 212, pass through the dichroic mirror 208 (which is configured to pass the fluorescence wavelength), and enter a first end 216 of a multi-core fiber optic cable 218. Photons that are emitted from the opposite side of chip 202 will be optionally focused by lens 220 and enter a second end 222 of fiber optic cable 218. The combined groups of photons will then be emitted from a third end 224 of fiber optic cable 218 and received by detection optic 226. The detection optic 226 can then collimate the combined emission from the two fiber optic cores and transmit the emission to one or more photodetectors (not shown) for measurement. In certain embodiments a series of dichroic and bandpass optical filters will be used to select specific wavelength bands and transmit them to a photodetector. In still further embodiments, separate detection optics may be used to capture the emitted photons instead using a multi core fiber optic cable.

Figure 3:
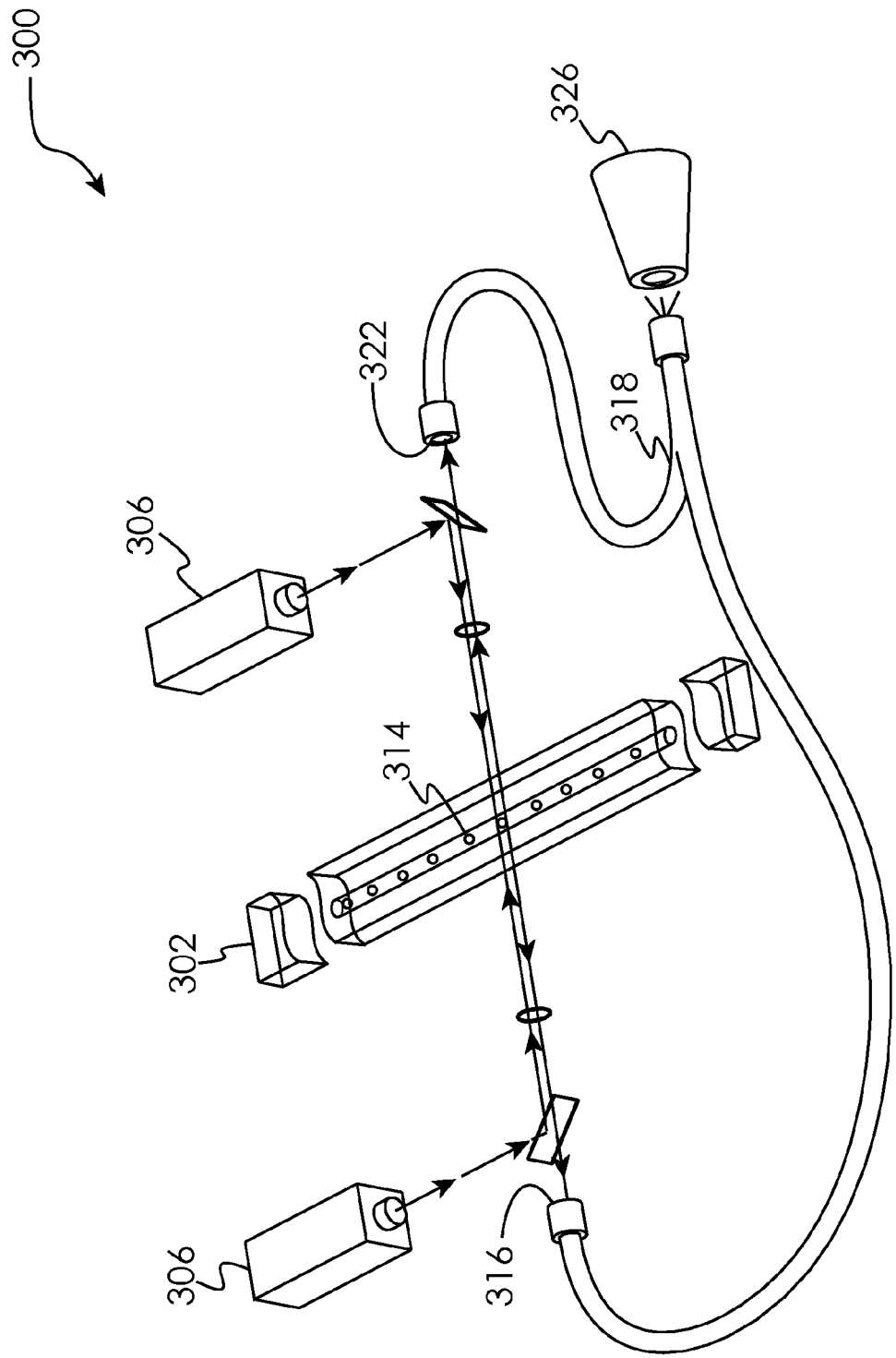
FIG. 3 is a schematic side view of a microfluidic device according to an embodiment of the present disclosure.

FIG. 3 schematically illustrates another embodiment of the present disclosure, shown here as system 300, in which multiple light sources 306 are used to generate fluorescence in the sample cells 314. In this embodiment, both the reflected and transmitted photons from the sample cells 314 will be detected from both sides of the cytometry chip 302. Again, the emitted photons will enter ends 316 and 322 of the fiber optic cable 318 and be captured by detection optics 326. In certain embodiments, the light sources 306 may be configured to generate different wavelengths of light. The detection optics can then detect different types of cells that have been dyed to fluoresce at the different wavelengths.

Microfluidic Device Using Spatial Intensity Modulation

Certain embodiments of the present disclosure are generally directed to systems for the analysis of a sample on a microfluidic device, using cytometry (such as flow cytometry or image cytometry). To increase overall cell throughput, multiple flow channels may be used in parallel to sort cells from a given sample. In such systems, the detection optics and associated electronic processing equipment must be able to distinguish between signals received from the individual channels. One way to accomplish this is to use individual excitation light sources on each channel, each with their own wavelength. However, this adds significant cost and complexity to the system. A single light source may also be scanned from channel to channel in a repeating fashion, with the detection optics determining which channel was scanned based on time. However this approach is also prone to errors due to the possibility of cells passing through the detection region of a given channel while the light source is exciting the detection region of a different channel.

As disclosed herein, another way to distinguish the separate channel fluorescence signals is to direct a single excitation light source on all of the channels simultaneously, but spatially vary or shape the excitation beam pattern so that a different excitation pattern is directed to the detection region of each channel. As a cell passes through the beam pattern of a particular channel, a series of time-spaced peaks will be created in the emitted fluorescence signal. Because the flow rate or speed of the cell is known, the time between the peaks, or frequency, can be used to determine which channel produced the signal. The detection optic is able to receive signals from all channels simultaneously and use varying means known in the art, such as frequency modulation/demodulation to separate and analyze the individual channel signals.

Various methods known in the art may be used to spatially vary the excitation beam within the detection region of each channel. In one embodiment, an optical element, such as a hologram or other light shifting device may be molded into the substrate of a microfluidic cytometry chip. The optical element transforms the uniform beam into spatial patterns within the detection regions of each channel. In other embodiments, the surface of the chip can be etched or coated with a non-reflective material to create the contrasting pattern elements. In still further embodiments, various mirrors, filters, or other light blocking or phase shifting means can be used to create the patterns. In still further embodiments, an active element such as a spatial light modulator or acousto-optic modulator may be employed to deliver time-varying spatial intensity patterns within the detection region of each channel. These spatial patterns may be dynamically altered at a faster rate than the progression of the cells passing through the detection region.

Figure 4:
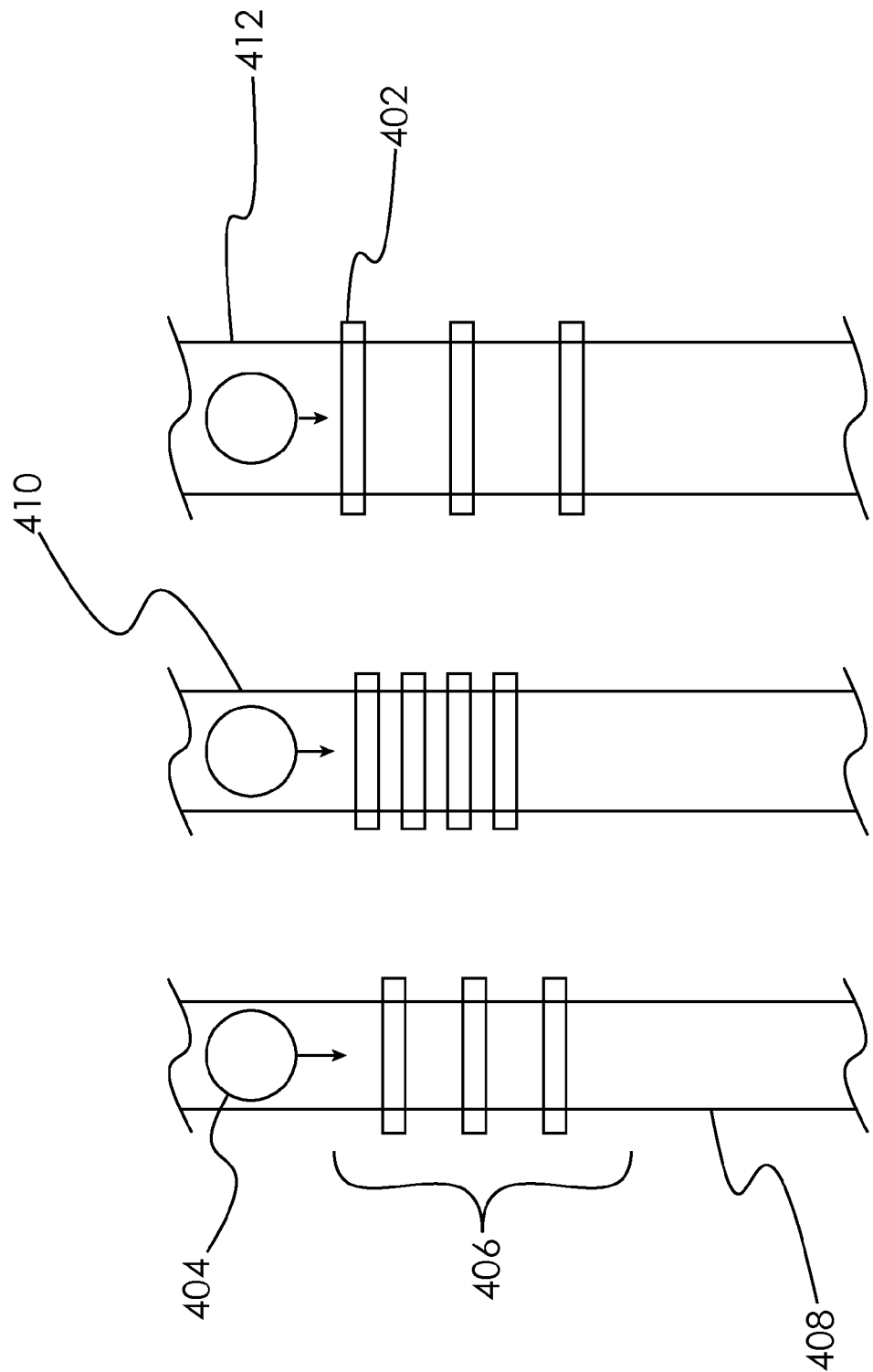
FIG. 4 is a schematic view of parallel flow cytometry channels having a spatially varied excitation pattern according to one embodiment of the present disclosure.

FIG. 4 schematically illustrates one embodiment where the excitation light patterns consist of a series of bars 402 spaced parallel to the direction that cells 404 are flowing through the detection region 406 of parallel flow channels 408, 410, and 412 within a microfluidic device. FIG. 5 illustrates sample resultant fluorescence signals 508, 510, and 512 for the channels 408, 410, and 412, respectively. As can be seen, varying the spacing between the bars 402 results in a unique signature in the fluorescence signal detected for each channel, thereby allowing the detection signal for any chosen channel to be separated from the detection signals produced by the other channels.

Figure 6:
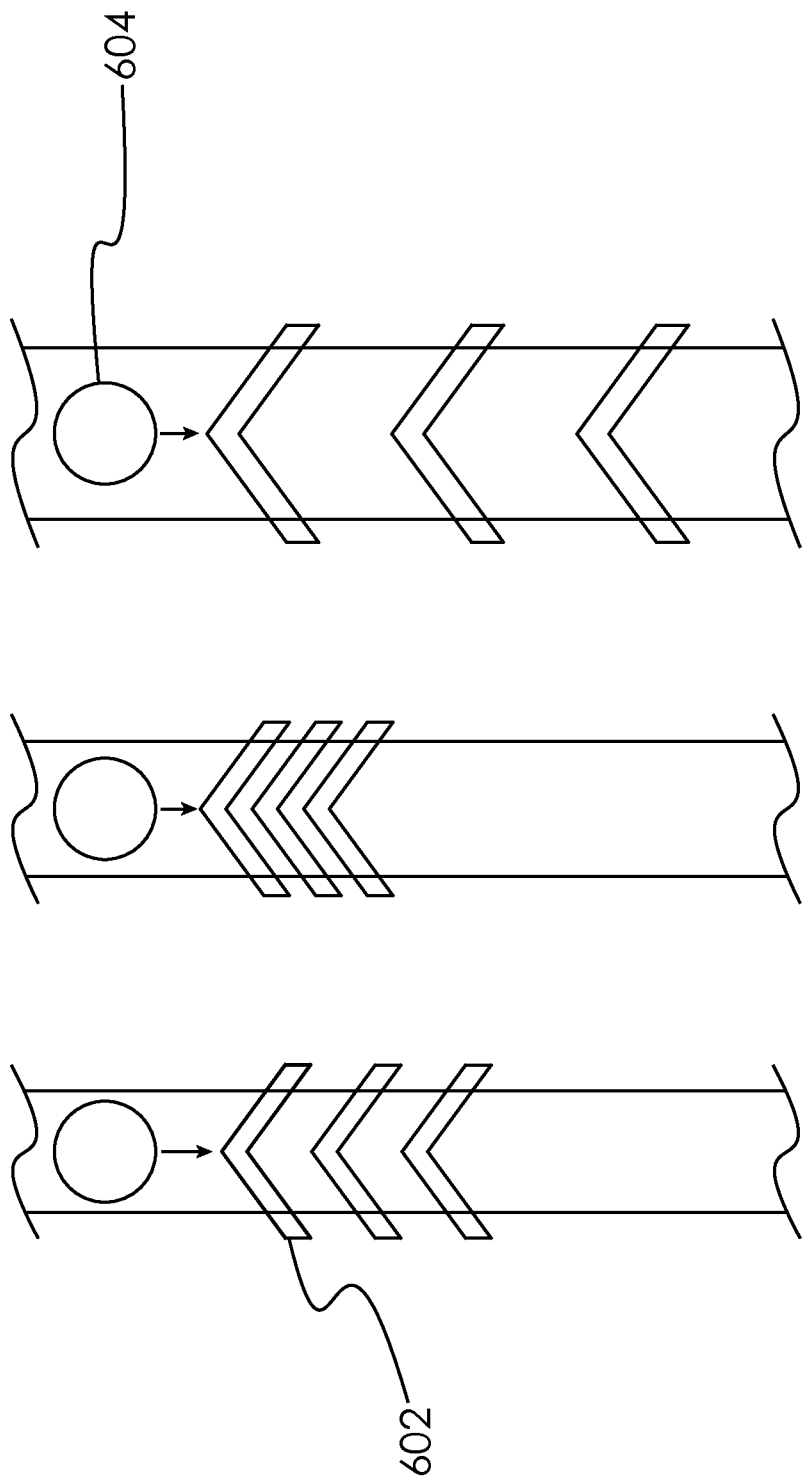
FIG. 6 illustrates a schematic view of parallel flow cytometry channels having excitation patterns which vary in two dimensions.

FIG. 6 shows another embodiment where the excitation pattern elements 602 vary perpendicular to the direction of flow in addition to varying parallel to the direction of flow. This allows the detection optics to received data about the cell 604 in two dimensions, as opposed to one. Using the two-dimensional fluorescence information produced as the cell 604 passes through the detection region, in conjunction with the particular mathematical function or shape of the pattern elements 602, a two dimensional image of the cell can be created, thereby providing much more information about the cell.

Microfluidic Device Having Magnetic Field Separator

Certain embodiments of the present disclosure are generally directed to systems for the separation and analysis of a biological sample on a microfluidic device using cytometry (such as flow cytometry or image cytometry) using an electromagnetic field. In order to increase the efficiency of cell sorting operations, it is desirable to start with a sample containing only those types of cells that are desired to be studied or isolated. One method known in the art is to subject the sample to centrifugation prior to cytometry analysis. After centrifugation, the sample components will be separated into layers. The desired component can then be easily extracted. However, this introduces the possibility that the sample layers will become remixed during the transfer from the initial collection vessel to the microfluidic device. By providing the separation capabilities integral with the microfluidic device itself, the possibility of layer mixing after centrifugation is reduced. This also eliminates the need for multiple containers and reduces the possibility of outside contaminates being introduced into the sample (or potentially harmful sample components being released into the outside environment).

Figure 7:
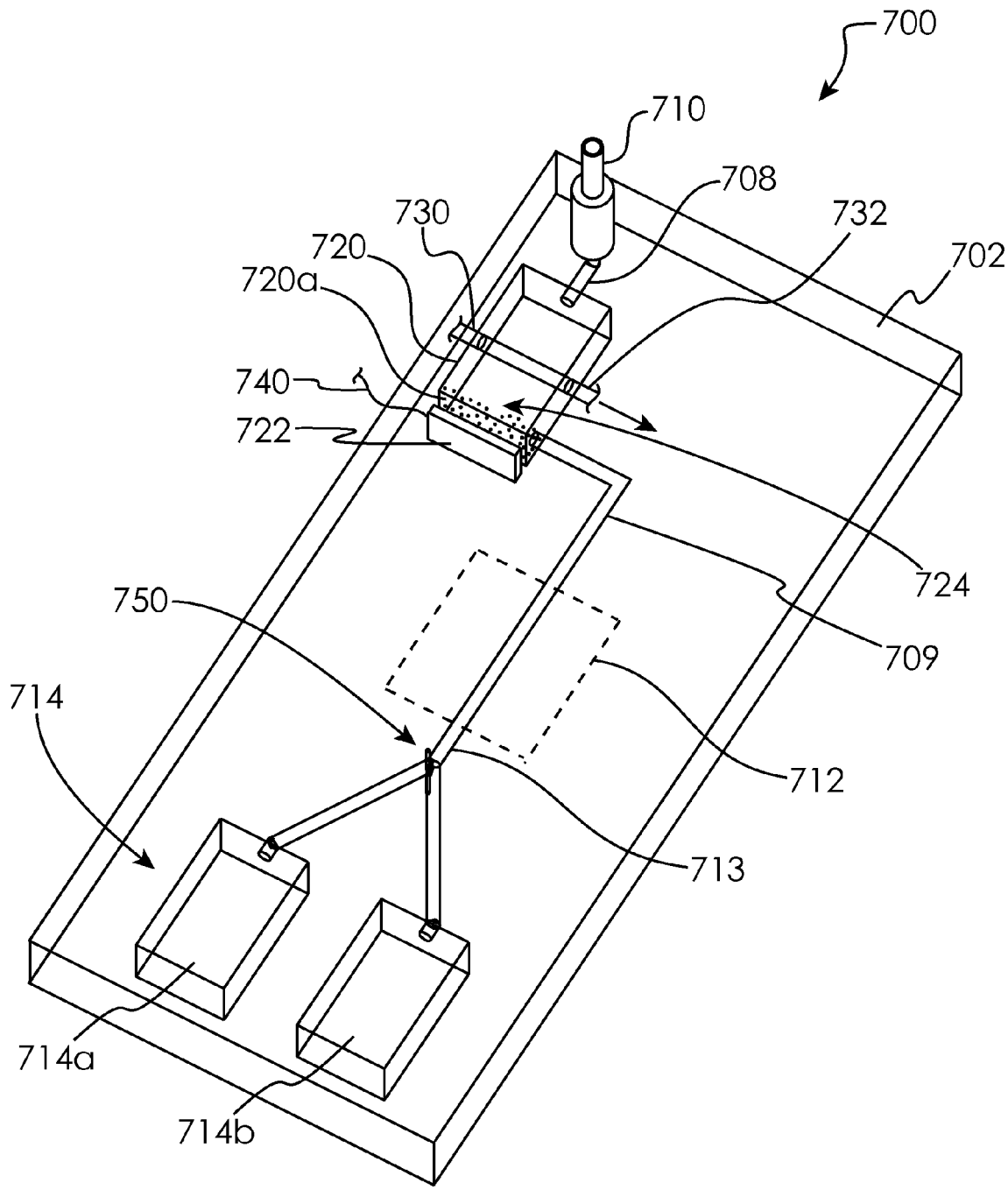
FIG. 7 is a schematic perspective view of a microfluidic device according to an embodiment of the present disclosure.

FIG. 7 schematically illustrates a microfluidic device 700 operable to achieve the separation of desired biological components contained with a biological sample. In the particular illustrated embodiments, cells from a cell supply (not shown) are input to input port 710 are initially separated at sample well 720 on substrate 702 due to an electromagnetic force. Thereafter, the separated cells are analyzed via cytometry in analysis section 712 (the specific operations that occur in analysis section 712 are not critical to the present disclosure). According to the results of the analysis performed, the cells may be sorted into different chambers 714. For simplicity and ease of illustration, FIG. 7 shows single channels extending between the components, areas or sections of chip 702. However, it should be appreciated that the single channels may be representative of multiple cytometry channels and a variety of possible configurations of channels as would occur to one skilled in the art.

Prior to their entry into the sample well 720, the cells that the researcher or medical professional desires to analyze via cytometry may each be coupled with a magnetic particle, either in addition to or in lieu of the attachment of a fluorescent molecule to the desirable cell. The magnetic particles used in accordance with system 700 may be sub-micron magnetic beads or other appropriate magnetic particles as would occur to one of ordinary skill in the art. The biological sample from input port 710 is received in sample well 720 via flow channel 708. Adjacent sample well 720 is an electromagnet 722 operable to create an electromagnetic field having an electromagnetic force within the sample well. In some embodiments, the electromagnet 722 may be temporarily, semi-permanently or permanently disposed onboard substrate 702. In other embodiments, the electromagnet 722 is brought into proximity with sample well 720 without being disposed onboard, attached to, or connected with chip 702. Electromagnet 722 may be self-contained such that the electrical energy to the electromagnet is through the use of batteries or other appropriate manners. In other embodiments, a power supply cord 740 is coupled to the electromagnet 722 to provide electrical energy thereto. In certain embodiments, the electromagnet 722 used to provide the magnetic field may be permanently positioned. The electromagnet may be mechanically moved into place when it is necessary to establish the magnetic field and moved out of place when it is necessary to remove the magnetic field.

The cells 724 to which the magnetic particles are coupled, as mentioned above, will enter the electromagnetic field, be attracted to electromagnet 722 and thus will be pulled toward the bottom of sample well 720 adjacent bottom surface 720a under the electromagnetic force. In certain embodiments, the sample well 720 is in flow communication with channel 709 leading to analysis section 712 at a location adjacent bottom surface 720a. In such embodiments, the initially separated group of cells 724 (those tagged with magnetic particles) will flow into channel 709 and into analysis section 712. To accomplish the travel of cells 724 into channel 709, the power to electromagnet 722 may be temporarily, semi-permanently or permanently reduced or eliminated and thus the electromagnetic force will be correspondingly reduced or eliminated. Accordingly, with the force reduced or eliminated, the cells 724 will be free to travel into channel 709 leading to analysis section 712. In some embodiments, the magnet 722 is strong enough to hold cells 724 at the bottom of well 720 until the magnetic force is reduced.

In another embodiment, the magnet 722 is not an electromagnet, but rather a permanent magnet. In this embodiment, the magnetic force due to magnet 722 may be overcome simply by the force of the sample fluid flow including cells 724 into channel 709 such that the cells 724 will exit the sample well 720. In other embodiments, the physical location or magnetic strength of magnet 722 is altered to reduce or eliminate the magnetic force on cells 724 a sufficient amount so that the cells 724 will flow out of well 720 into channel 709 leading to analysis section 712. In some embodiments, the magnet 722 is strong enough to hold cells 724 at the bottom of well 720 until the magnetic force is reduced.

Additionally, sample well 720 may optionally include input and waste ports 730 and 732, respectively, for the introduction and removal of a wash fluid. The wash fluid may remove unwanted or undesirable material from the sample well prior to entry into the cytometry analysis. In such embodiments, as the wash fluid travels through sample well 720 via ports 730 and 732, the wash fluid may force, push or direct the material in the biological sample that is not attracted to electromagnet 722 out through waste port 732. In certain embodiments, the non-magnetized material from the biological sample will remain suspended in sample fluid and the force of the wash fluid moving through sample well 720 will cause the non-magnetized material to exit the well. Accordingly, the non-magnetized material is prevented from entering the cytometry analysis, thereby providing an initial step of sample purification prior to analysis and sorting. In such embodiments, the electromagnetic force pulling the cells 724 toward bottom surface 720a of well 720 is greater than the force of the wash fluid moving through well 720 such that the cells 724 are not washed out through waste port 732.

After the separated cells 724 are analyzed in section 712, the cells may travel through channel 713 and optionally be sorted into the different wells or chambers 714 based on differing characteristics of the cells. In certain embodiments, the sample wells 714 have outlet ports (not shown) in fluid communication therewith in order to facilitate removal of the sorted sample from the wells. Sample fluid may be diverted to wells 714 by appropriate control of flow diverter 750.

In one embodiment, the flow diverter 750 is a piezoelectric device that can be actuated with an electric command signal in order to mechanically divert the flow through the sorting channel 713 into either the well 214a or the well 214b, depending upon the position of the flow diverter 750. In other embodiments, flow diverter 750 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

Cells may be sorted into different wells or chambers 714 based on the intended future use for the cells. For example, cells having the same characteristics, or phenotype, may be sorted into one well where they are fixed for viewing, and sorted into another well where they are maintained in a viable state to undergo additional functional measurements. As another example, desirable cells may be sorted into an extraction well or chamber and undesirable cells may be sorted into a waste well or chamber. Alternatively, the cells may be deposited into the wells or chambers based on volume as opposed to a sorting method. The chip may include means for physically diverting the cells into the chambers 714 from the analysis section 712 as is known in the art. Alternatively, the cells may be caused to exit the chip 702 after the analysis is complete.

By initiating a pre-analysis and pre-sorting separation method, system 700 allows the researcher or medical professional to increase the purity of the finally sorted cells as opposed to systems which provide only for analysis and sorting. This can be especially advantageous when sorting desirable stem cells through cytometry analysis because of the generally low concentration of stem cells in a biological sample and their high desirability.

The sample well 720 may take any convenient physical form, such as a well formed into the surface of substrate 702 which may be closed, may remain open and/or may include a cover. The sample well 720 is shown as being positioned near the top of the chip; however, it should be appreciated that the sample well may be positioned elsewhere on the substrate.

Stackable Microfluidic Devices

In certain embodiments, the present disclosure is generally directed to stackable microfluidic devices. Providing microfluidic devices in a stackable arrangement can help to protect the devices themselves from scratching, abrasion or other unwanted irritation. Stacking the microfluidic devices according to the present disclosure also helps to prevent the microfluidic devices from sticking together by separating the flat front and back surfaces of the devices. Furthermore, the embodiments disclosed herein facilitate stacking of microfluidic devices that have one or more non-flat surface. For example, one surface may have a lens attached thereto, portions of which extend out of the plane of the substrate surface. Additionally, the stackable arrangement may make it easier for a researcher, medical professional or other user to grip and manipulate the devices. It further may facilitate the use of automation and/or robotic elements to handle the microfluidic devices.

Figure 8:
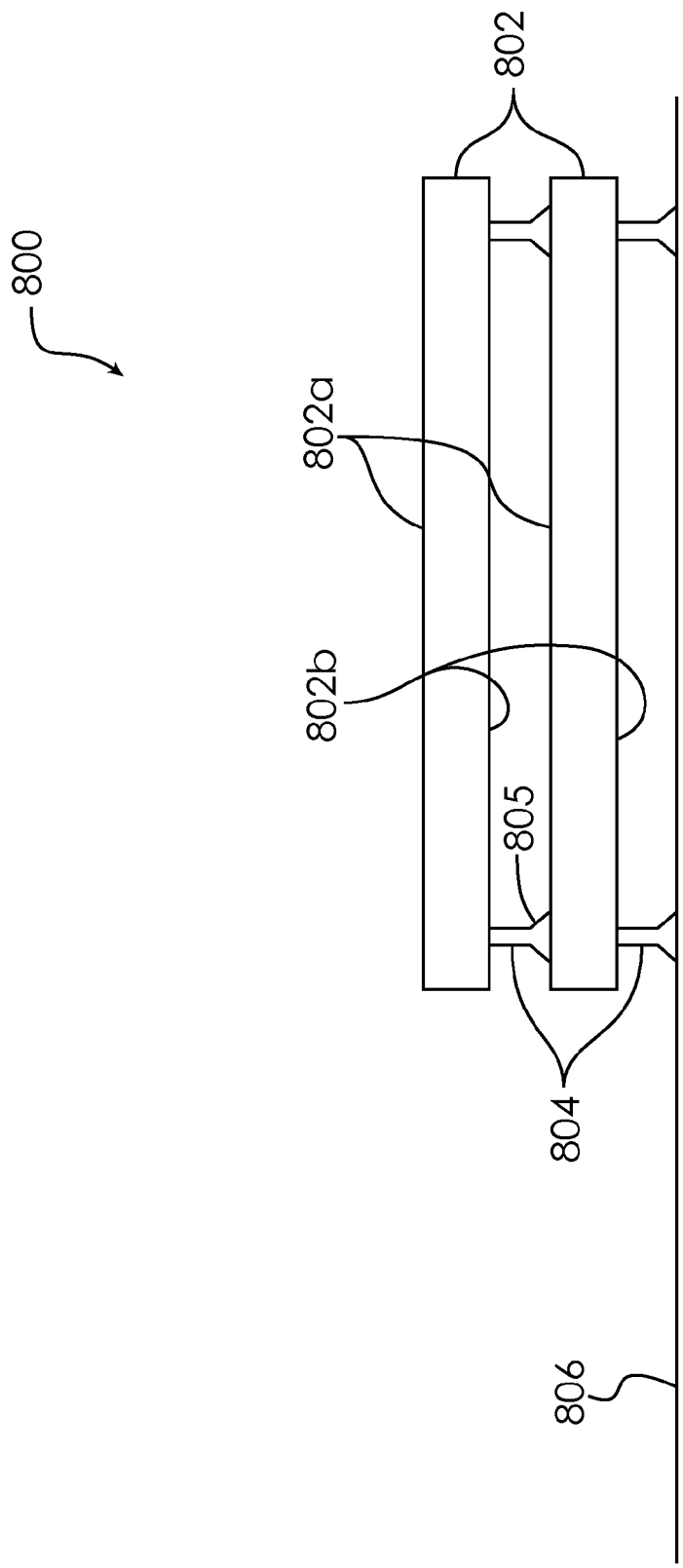
FIG. 8 is a schematic side view of a stack of microfluidic devices according to an embodiment of the present disclosure.

FIG. 8 schematically illustrates microfluidic devices, such as cytometry chips 802, in a stacked arrangement 800. The cytometry chips 802 may be generally designed so that material from a biological sample may be analyzed thereon via cytometry (the specific operations that occur in the cytometry analysis are not critical to the present disclosure). In certain embodiments, the cytometry analysis may include image cytometry or flow cytometry, as examples. According to the results of the analysis performed, the material in the sample may optionally be sorted into one or more different wells or chambers disposed on the chips 802. Alternatively, the cells may be caused to exit the chips 802 after the analysis is complete. It should be appreciated that the various cytometry components and sections of the chips 802 are not illustrated for simplicity and can vary greatly as would occur to one of ordinary skill in the art.

Figure 9:
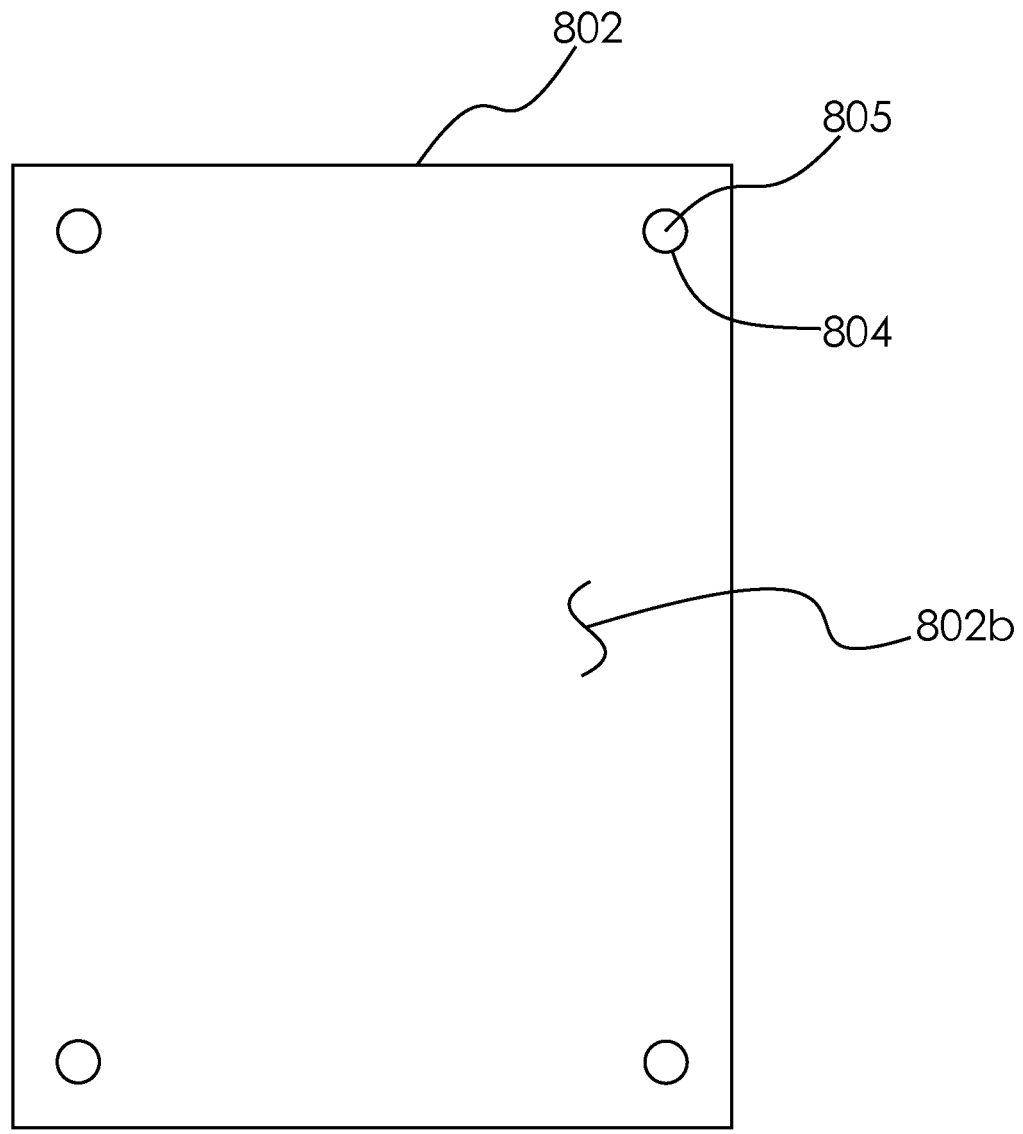
FIG. 9 is a schematic bottom view of a microfluidic device according to the embodiment of FIG. 8.

In certain embodiments, the cytometry analyses may occur with respect to front or top surfaces 802a of the chips 802 and legs 804 may be attached to the back or bottom surfaces 802b of the chips 802 to allow the chips to be stacked on top of each other. In the illustrated embodiment, each chip 802 is generally rectangular in shape and includes four legs 804 extending down from surface 802b and positioned near the four corners of the device, as best illustrated in FIG. 9. However, it should be appreciated that the legs 804 can number more or less than four on each chip 802 and/or can be positioned at other locations on the chip 802 as would occur to one of ordinary skill in the art. In certain embodiments, the legs 804 are positioned at certain locations on each chip 802 so that they do not interfere with any of the cytometry components or sections on surface 802a of an adjacent chip 802 when in the stacked arrangement 800.

Figure 10:
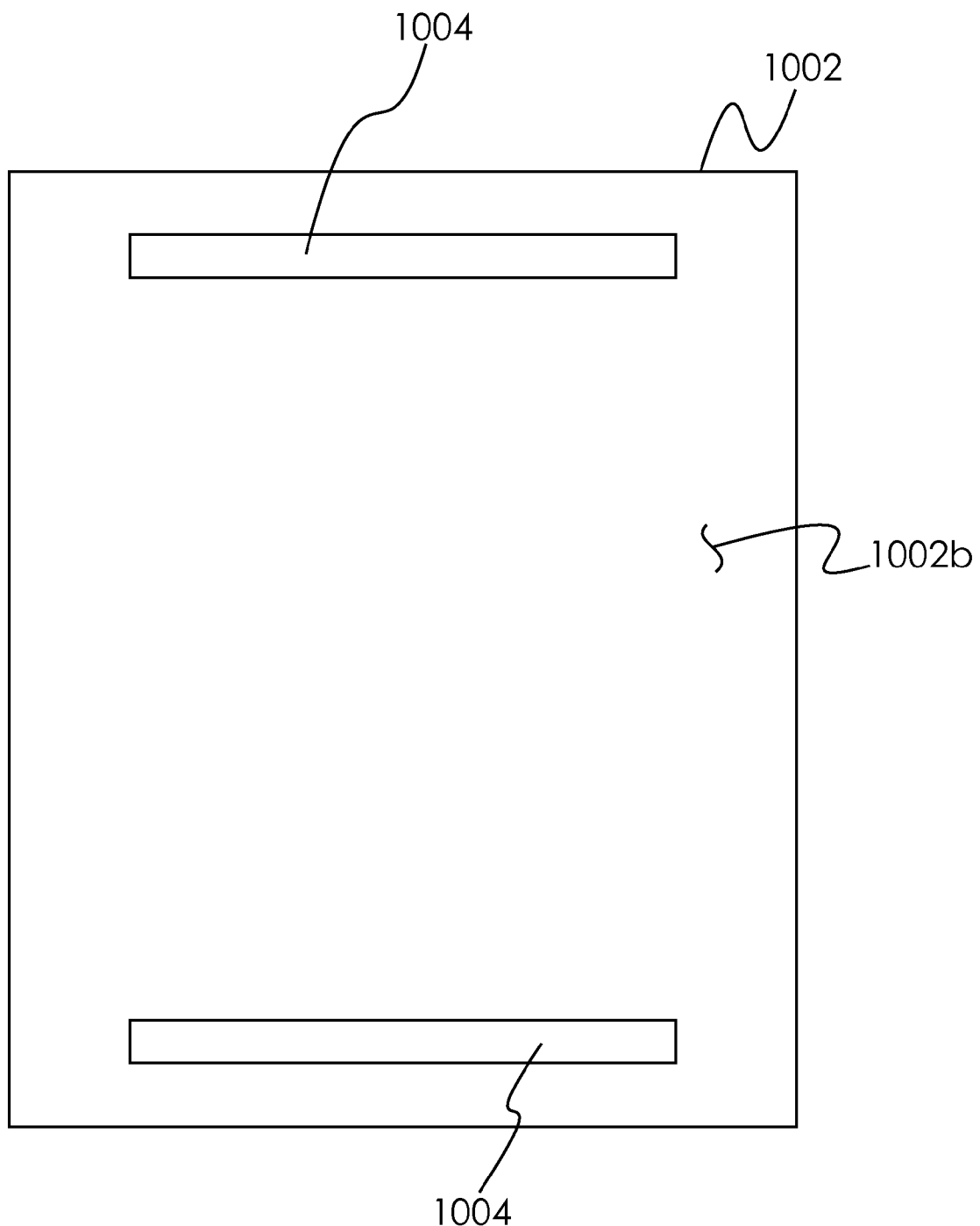
FIG. 10 is a schematic bottom view of a microfluidic device according to an embodiment of the present disclosure.

In the illustrated embodiment, each leg 804 is attached to or integral with surface 802b at one end and includes a widened foot portion 805 at the other end. Additionally, the illustrated legs 804 are substantially cylindrical with circular cross-sectional shapes. Each foot portion 805 includes a larger diameter than the remainder of leg 804 to provide additional stability to the stacking arrangement 800. However, it should be appreciated that the chips 802 and/or the legs 804 can be shaped differently than as illustrated. As an example, foot portions 805 may be absent such that the legs 804 have a constant diameter throughout their lengths. As another example, legs 804 may include cross-sectional shapes that are square or rectangular. For example, in an alternative embodiment the chips 1002 may each include a single rectangular foot 1004 at opposite ends thereof, as illustrated in FIG. 10. It should be appreciated that the legs 804, 1004 are just two non-limiting examples of numerous possible stacking elements as would occur to one of ordinary skill in the art that can be incorporated into a microfluidic device.

Microfluidic Device Having 3-D Hydrodynamic Focusing to Align Sperm Cells

In certain embodiments, the present disclosure is generally directed to a microfluidic device capable of 3-D hydrodynamic focusing to align sperm cells in a flow channel in the device. The device includes sheath fluid sub-channels joining with a sample cytometry channel having sperm cells traveling therein, the sub-channels being positioned in two different planes to three-dimensionally align the sperm cells in the sample channel in the proper orientation for a cytometry analysis.

Figure 11:
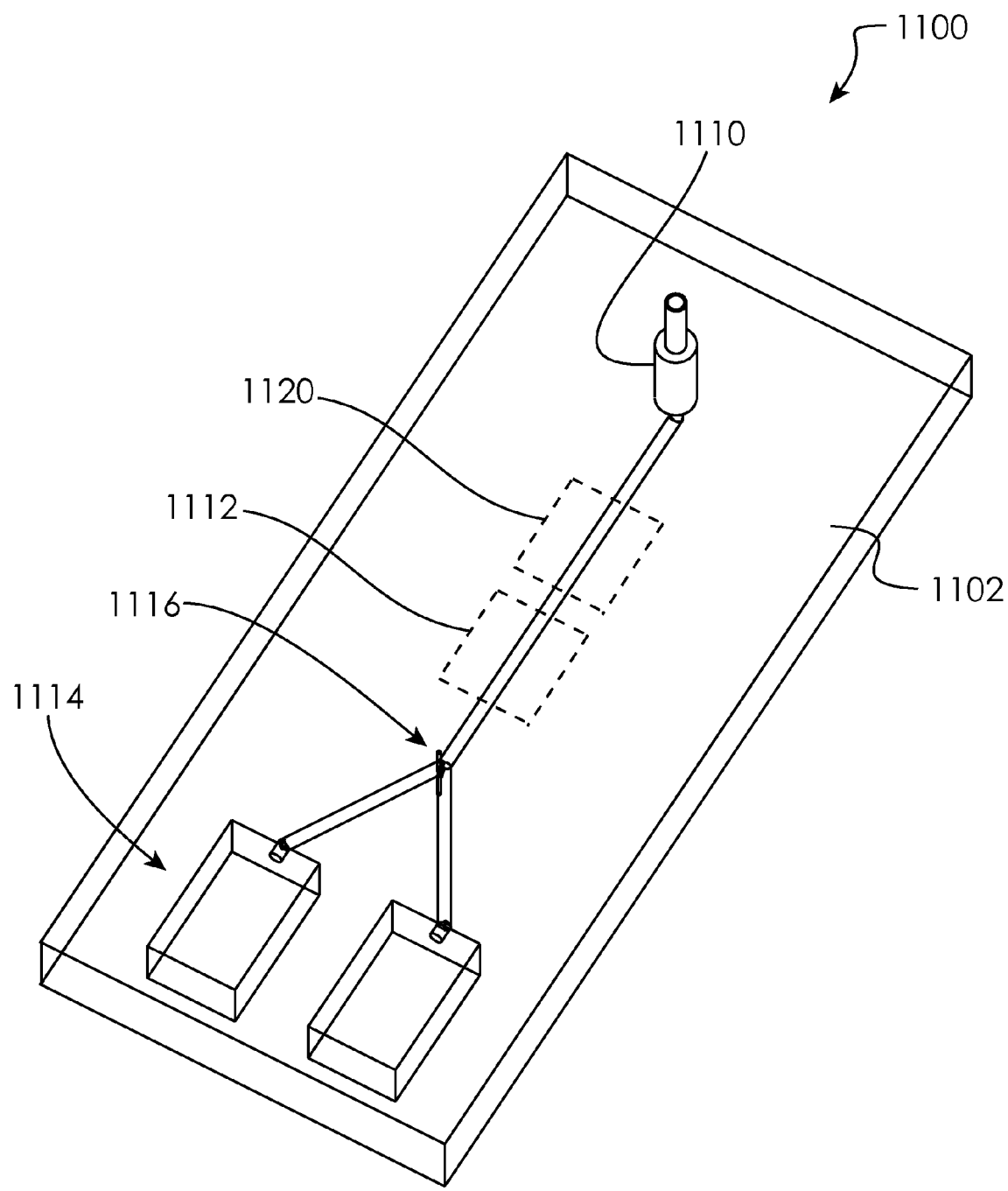
FIG. 11 is a schematic perspective view of a microfluidic device according to an embodiment of the present disclosure.

FIG. 11 schematically illustrates a microfluidic device 1100 formed on a substrate 1102 on which cells, such as sperm cells, from a biological sample (not shown) input to input port 1110 are aligned in section 1120 (as will be described in greater detail below) and analyzed via cytometry (such as, for example, flow cytometry or image cytometry) in analysis section 1112 (the specific operations that occur in analysis section 1112 are not critical to the present disclosure). According to the results of the analysis performed, the cells may optionally be sorted into one or more different wells or chambers 1114. In certain embodiments, the sample wells 1114 have outlet ports (not shown) in fluid communication therewith in order to facilitate removal of the sorted sample from the wells. Sample fluid may be diverted to wells 1114 by appropriate control of flow diverter 1116.

In one embodiment, the flow diverter 1116 is a piezoelectric device that can be actuated with an electric command signal in order to mechanically divert the flow through the flow channel into either of the wells 1114, depending upon the position of the flow diverter 1116. In other embodiments, flow diverter 1116 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

It should be appreciated that various components and sections shown on the chip 1100 are intended to show the operations of the cytometry process in a simple schematic form and the cytometry components and sections on the chip 1100 can vary greatly as would occur to one of ordinary skill in the art.

The cells may be sorted into the different chambers 1114 based on differing characteristics of the cells. Cells may be sorted into the different chambers 1114 based on the intended future use for the cells. For example, cells having the same characteristics, or phenotype, may be sorted into one chamber where they are fixed for viewing and sorted into another chamber where they are maintained in a viable state to undergo additional functional measurements, or properly stored for use as part of a cell-based therapeutic procedure. In a specific embodiment, sorted and isolated sperm cells may be used for artificial insemination or in-vitro fertilization for both humans and animals. Such medical procedures may be used in cases of infertility and to prevent sex-linked gene-propagated diseases from passing to a new generation. As another example, desirable cells may be sorted into an extraction well or chamber and undesirable cells may be sorted into a waste well or chamber. Alternatively, the cells may be deposited into the chambers 1114 based on volume as opposed to a sorting method. Alternatively, the cells may be caused to exit the chip 1100 after the analysis is complete.

For simplicity, the illustration of FIG. 11 shows two chambers 1114; however, it should be appreciated that the microfluidic device may include more or less than two chambers as would occur to one of ordinary skill in the art. Additionally, the chambers 1114 are shown as being horizontally aligned near the bottom of the substrate 1102. However, it should be appreciated that the chambers 1114, if present, may be positioned at other locations on the substrate 1102 as would occur to one of ordinary skill in the art. Additionally, for simplicity and ease of illustration, FIG. 11 shows single channels extending between the components, areas or sections of substrate 1102. However, it should be appreciated that the single channels may be representative of multiple cytometry channels and a variety of possible configurations of channels as would occur to one skilled in the art.

FIGS. 12A and 12B show an example sperm cell 1104 which may be introduced into input port 1110 for cytometry analysis, with FIG. 3A showing a top view and FIG. 3B showing a side view. In certain embodiments, the sperm cell 1104 includes a head 1105 and a tail 1106. As illustrated, the heads of some sperm cells are typically pancake-shaped with their width W larger than their thickness T. For the purposes of cytometry analysis, it can be beneficial to analyze the cell from the top, as it is oriented in FIG. 3A, as more information can be gained because more of the cell via its width W is available for analysis.

Figure 13:
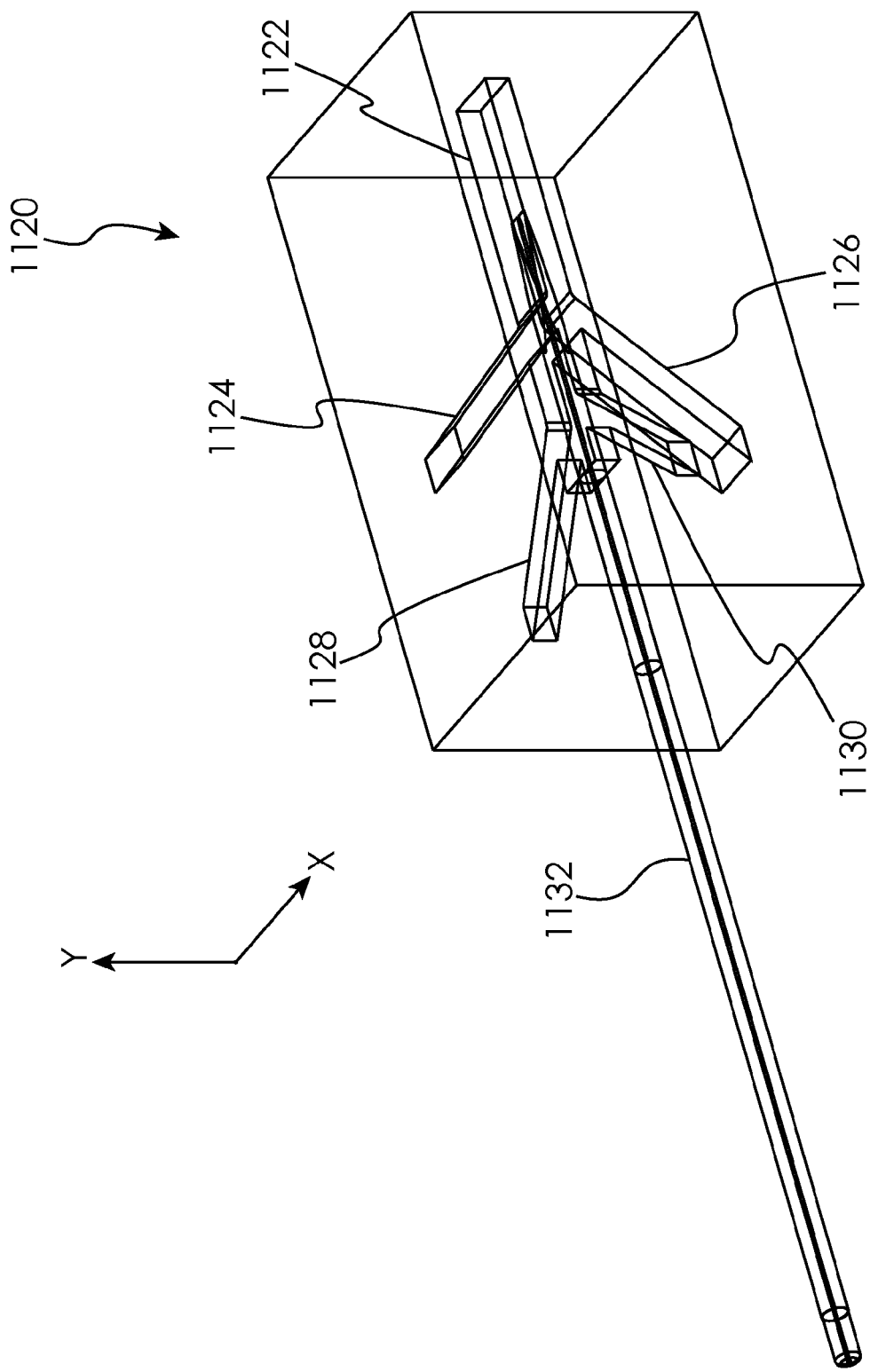
FIG. 13 is a schematic perspective view of a section of a microfluidic device according to an embodiment of the present disclosure.

Accordingly, it can be desirable to orient the sperm cell 1104 such that the full width W is available for analysis prior to entry into the cytometry analysis section 1112. This orientation provides the most uniform illumination of the cell 1104 as it passes through the analysis section 1112 of the device. For most mammalian species, this orientation is necessary to obtain the precision needed to measure the DNA difference between sperm cells that will produce females and sperm cells that will produce males. To accomplish this, chip 1100 can include a hydrodynamic focusing section, such as alignment section 1120, to properly orient the sperm cell 1104 (see FIG. 13). Section 1120 may be operable to align sperm cells entering sample channel 1122 from sample injection tube 1132, the injection tube being coupled with biological sample 1110. As illustrated, section 1120 includes sheath entry sub-channels 1124 and 1126 in the same plane, such as plane Y, and sheath entry sub-channels 1128 and 1130 in the same plane, such as plane X which is orthogonal to plane Y, to properly align and orient sperm cells flowing through sample channel 1122. The sheath entry sub-channels are configured such that sheath fluids from each sub-channel into the sample channel 1122 work in combination to align and orient the sperm cells in the channel 1122. In the particular illustrated embodiment, sub-channels 1124 and 1126 are larger in cross-sectional dimension than sub-channels 1128 and 1130 such that a greater amount of sheath fluid may enter channel 1122 from those locations than the amount of sheath fluid which enters from sub-channels 1128 and 1130. Accordingly, in the particular illustrated embodiment, the sheath fluid will cause the sperm cells to be aligned with their larger width dimension generally in the X plane and their smaller thickness dimension generally in the Y plane. Additionally, the sheath flow sub-channels 1124, 1126, 1128, and 1130 may also function to position the sperm cells at the center of the channel 1120 to better ensure that the cells pass through the focus of the optic system that may be part of the cytometry analysis.

The proper orientation is enhanced by the used of the tube 1132 which has a beveled end, the flat surfaces of the beveled end being aligned with or facing the incoming sheath flow entering from sub-channels 1124 and 1126. This system will produce laminar flow between the core sample stream of sperm cells emerging from the end of the beveled tube 1132 and the sheath fluid passing over the end of the tube 1132. The core sample stream will remain asymmetrical, having a greater width measured in the x direction than height measured in the y direction, as it passes through the analysis section 1112 of the chip 1100. This asymmetry will enable the sperm cells to remain properly oriented as they pass through the analysis section 1112.

It should be appreciated that the section 1120 may be an integral portion of substrate 1102 or may be attached to the substrate 1102 in an appropriate manner as would occur to one of ordinary skill in the art. In alternative embodiments, section 1120 may be separate from the substrate 1102, with a channel connecting the output of section 1120 with a flow channel on the substrate 1102.

Microfluidic Device Having Acoustic Energy Coupler

Certain embodiments of the present disclosure are generally directed to a microfluidic device having an acoustic energy coupler positioned within a component of the microfluidic device to disrupt the cells contained in the component. Disruption of the cells may cause the internal molecular material within the cells to be released so that the material may be observed or tested by a researcher or medical professional. In certain embodiments, the cells are sorted into a container following a cytometry analysis, such as flow or image cytometry as non-limiting examples.

Figure 14:
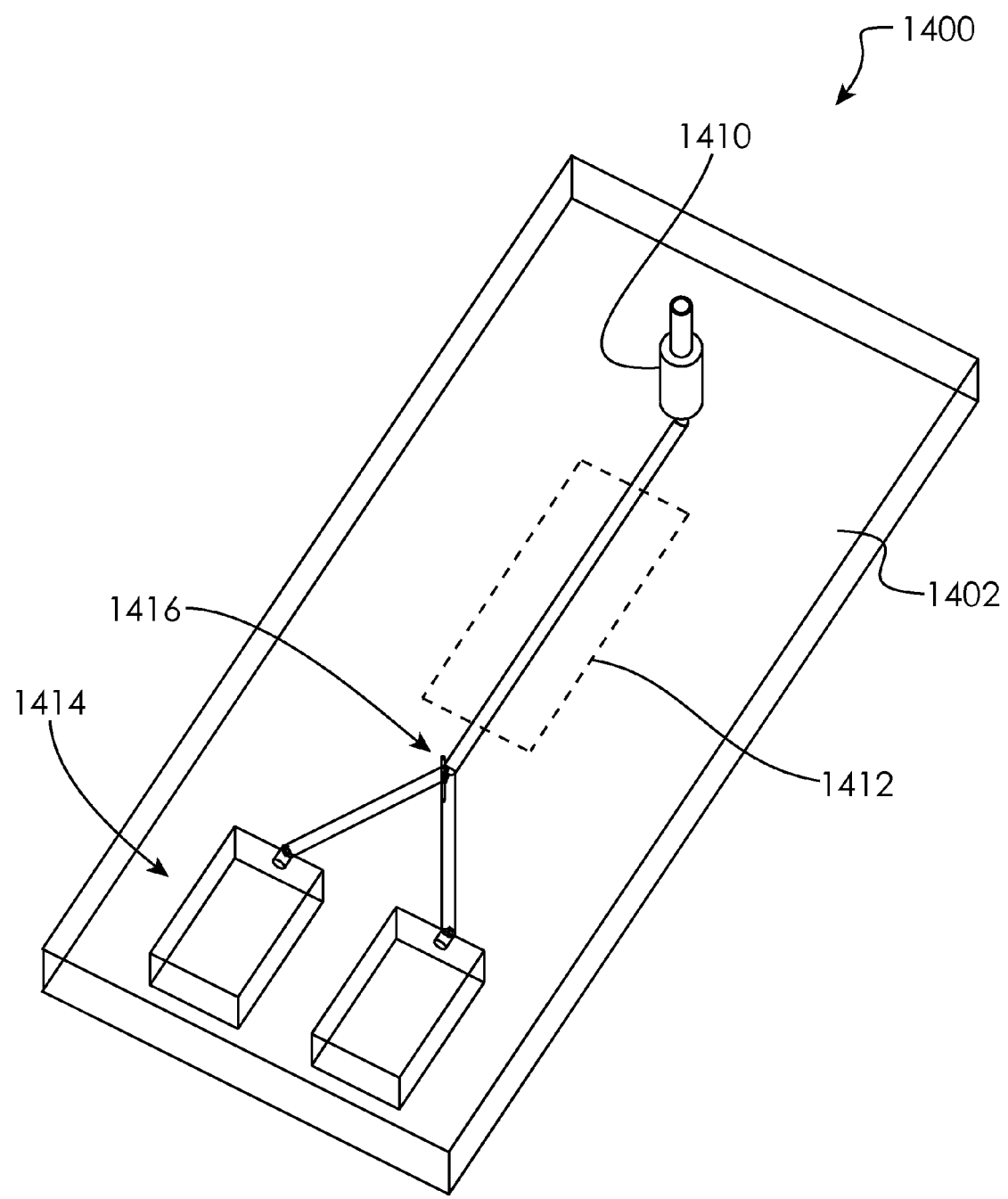
FIG. 14 is a schematic perspective view of a microfluidic device according to an embodiment of the present disclosure.

FIG. 14 schematically illustrates a microfluidic device 1400 formed on a substrate 1402, on which cells or other material from a biological sample (not shown) are input to input port 1410 are analyzed via cytometry (such as, for example, flow cytometry or image cytometry) in analysis section 1412 (the specific operations that occur in analysis section 212 are not critical to the present disclosure). According to the results of the analysis performed, the cells may optionally be sorted into one or more different wells or chambers 1414. In certain embodiments, the sample wells 1414 have outlet ports (not shown) in fluid communication therewith in order to facilitate removal of the sorted sample from the wells. Sample fluid may be diverted to wells 1414 by appropriate control of flow diverter 1415.

In one embodiment, the flow diverter 1415 is a piezoelectric device that can be actuated with an electric command signal in order to mechanically divert the flow through the flow channel into either of the wells 1414, depending upon the position of the flow diverter 1415. In other embodiments, flow diverter 1415 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

It should be appreciated that the various components and sections shown on the substrate 1402 in the illustration of FIG. 14 are intended to show the operations of the cytometry process in a simple schematic and the cytometry components and sections on the substrate 1402 can vary greatly as would occur to one of ordinary skill in the art.

The cells may be sorted into the different wells or chambers 1414 based on differing characteristics of the cells. Cells may be sorted into the different chambers 1414 based on the intended future use for the cells. For example, cells having the same characteristics, or phenotype, may be sorted into one chamber where they are fixed for viewing and sorted into another chamber where they are maintained in a viable state to undergo additional functional measurements, or properly stored for use as part of a cell-based therapeutic procedure. As another example, desirable cells may be sorted into an extraction well or chamber and undesirable cells may be sorted into a waste well or chamber. Alternatively, the cells may be deposited into the chambers 1414 based on volume as opposed to a sorting method. The chip may include means for physically diverting the cells into the chambers 1414 from the analysis section 1412 as is known in the art. Alternatively, the cells may be caused to exit the substrate 1402 after the analysis is complete.

For simplicity, the illustration of FIG. 14 shows two chambers 1414; however, it should be appreciated that the microfluidic device may include more or less than two chambers as would occur to one of ordinary skill in the art. Additionally, the chambers 1414 are shown as being horizontally aligned near the bottom of the substrate 1402. However, it should be appreciated that the chambers 1414, if present, may be positioned at other locations on the substrate 1402 as would occur to one of ordinary skill in the art. Additionally, for simplicity and ease of illustration, FIG. 14 shows single channels extending between the components, areas or sections of substrate 1402. However, it should be appreciated that the single channels may be representative of multiple cytometry channels and a variety of possible configurations of channels as would occur to one skilled in the art.

According to the present disclosure, at least one component on the chip 1400 includes an acoustic energy coupler to disrupt cells contained within the component. To illustrate an example, FIG. 15 shows an acoustic energy coupler 1416 in the form of a probe positioned within a chamber 1414. However, it should be appreciated that the acoustic energy coupler may be positioned in other components of the chip 1400, including an input well or other cell collection vessel on the chip. As illustrated, acoustic energy coupler 1416 vibrates or oscillates in response energy received from acoustic energy source 1420. It should be appreciated that coupler 1416 may be sized, shaped and/or otherwise configured differently and/or orientated differently in chamber 1414 than as illustrated as would occur to one of ordinary skill in the art.

In certain embodiments, sample fluid having cells suspended therein is collected within chamber 1414. Acoustic energy coupler 1416 is operable to vibrate within the sample fluid in response to acoustic energy that it receives from source 1420 to disrupt the cells. The acoustic energy transferred to coupler 1416 may be in the form of sound energy (such as, for example, ultrasonic energy) so that a process of sonication may be applied to the sample fluid to agitate the cells therein. In some embodiments, coupler 1416 is operable to vibrate or oscillate at its resonance frequency (corresponding to its maximum amplitude) to provide optimum disruption to the cells.

In certain embodiments, the disruption to the cells is of sufficient intensity to break the cell members and release the inner molecular material of the cells into the sample fluid. The inner molecular material can then be observed or tested by a researcher or medical professional. Additionally, in the illustrated embodiment the cells are disrupted following the cytometry analysis and the sorting of the cells into the chamber 1414. However, it should be appreciated that the coupler can be placed in a different chip component which houses cells prior to the cytometry analysis, such as an initial cell repository. After the cells are disrupted and the molecular material is released in the initial cell repository, the molecular material can be caused to enter section 1412 for cytometry analysis.

In certain embodiments, acoustic energy source 1420 is separate from coupler 1416 and may be incorporated with the external instrument system conducting the cytometry analysis with respect to the biological sample on the chip 1400. In other embodiments, the acoustic energy source 1420 may be separately applied to the chip 1400 following completion of the cytometry analysis and removal of the chip 1400 from the external system conducting the analysis.

Microfluidic Device Having Phase Variation Producing Lens

Certain embodiments of the present disclosure are generally directed to systems for the analysis of a sample on a microfluidic device such as a cytometry chip, using cytometry (such as flow cytometry or image cytometry). In order to detect or identify cells during cytometry operations, a source (such as a laser) of electromagnetic radiation (such as visible light) is directed to a detection area. When a cell passes through the detection area within a flow channel, the light source causes the cell to fluoresce. This effect may be enhanced by certain dyes which are added prior to the cell reaching the detection area as described hereinabove.

In certain applications, it may be necessary to incorporate various optical elements into the substrate of the device or chip to vary the light-scattering nature of the various surfaces. In particular, light-shaping optics such as holographic elements or free-form lenses and mirrors may be employed to deliver intensity/phase/polarization spatial patterns or other light shifting effects on various surfaces of the chip. Because such elements can be formed or etched into the chip substrate, there is little cost to reproduce them once the initial mold or etching program is designed. More particularly, the lens used to focus an incoming excitation light beam may also be manufactured such that it will also deliver particular spatial light pattern within the channel detection region.

Figure 16:
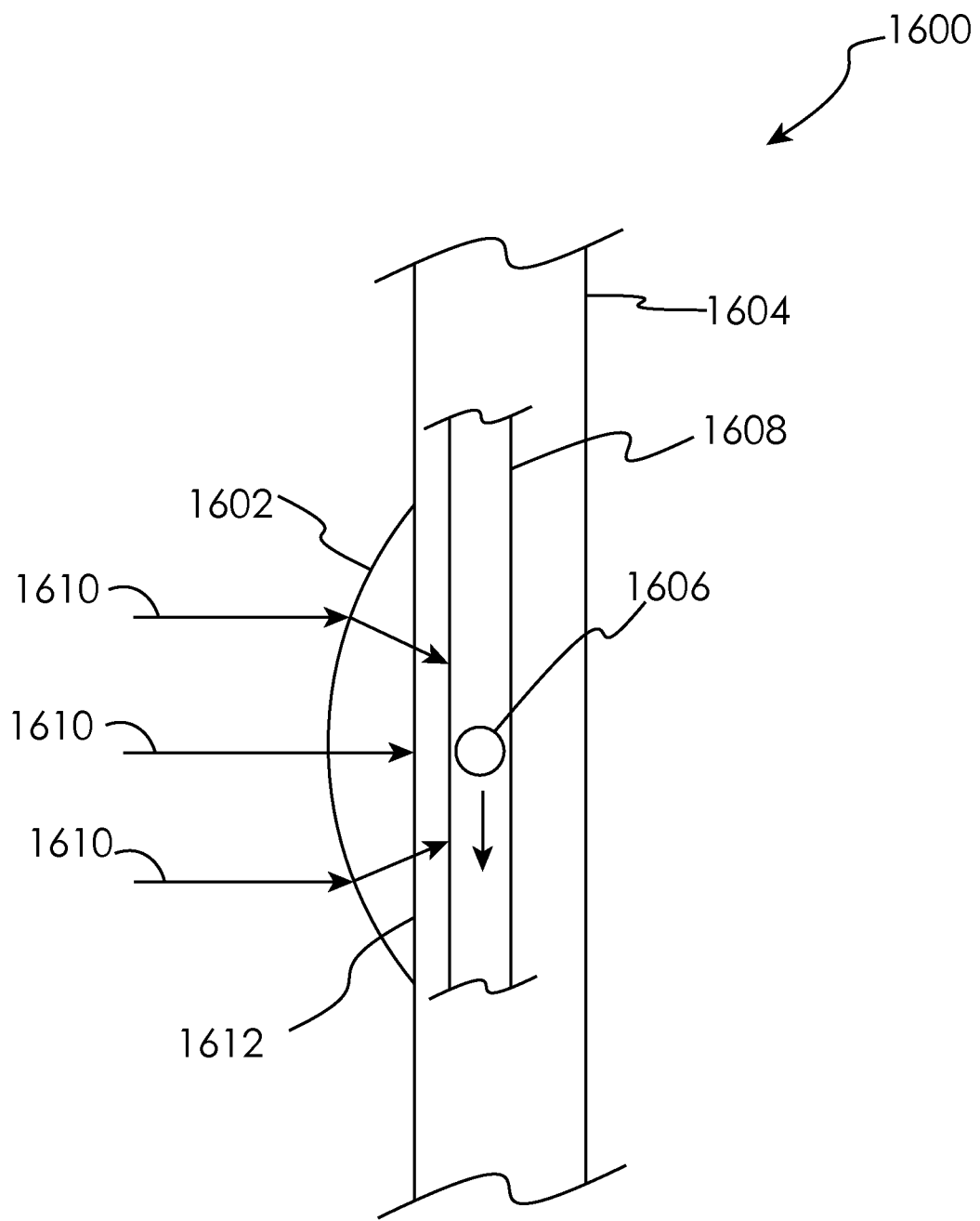
FIG. 16 is a schematic side view of a section of a microfluidic device according to an embodiment of the present disclosure.

FIG. 16 schematically shows one embodiment where a focusing lens 1602 is mounted to the surface of a microfluidic device 1600 substrate 1604. As a sample cell 1606 passes through the detection flow channel 1608, the excitation light 1610 is focused on the sample cell 1606. The surface 1612 of the focusing lens 1602 has been formed, etched, or otherwise treated such that it will impart spatially varied phase changes on the incoming excitation light 1610. The phase changes translate into an optical holographic effect on the detection region, which can be made to form a specific spatial pattern or design.

During manufacture of the focusing lens 1602, the surface 1612 can be coated with a UV sensitive material. A pulsed laser can then be used to scan the surface 1612 to expose the UV material and create small variations in the surface according to a desired pattern or image. When the focusing lens 1602 is later mounted to the substrate 1604 and receives the excitation light 1610, it will create a holographic effect within the detection channel 1608. In certain embodiments, the focusing lens 1602 may be made entirely of the UV sensitive material, as opposed to merely the surface 1612. In still other embodiments, the variations on the surface 1612 may achieved by injection molding or other means known in the art for reproducing holographic effects. In a similar fashion to holographic elements, other types of free-form lens and mirror shapes can also be combined with focusing lens 1602 by first constructing a master copy using micro-machining techniques known in the art such as diamond turning from a computer designed shape. This master copy can then be replicated using injection molding or other means known in the art.

The specific pattern or desired holographic effect may be selected for various uses. As one non-limiting example, the holographic lens or free-form optical element can be used to create spatially varied patterns to determine a unique "signature" for a detection channel. In order to increase overall cell throughput, multiple flow channels are often used in parallel to measure and/or sort cells in a cytometry device, such as a droplet cell sorter or a microfluidic device. In such systems, the detection optics and associated electronic processing equipment must be able to distinguish between signals received from the individual channels. One way to accomplish this is to direct a single excitation light source to all of the channels simultaneously, but spatially vary or shape the excitation beam pattern so that a different excitation pattern is directed to the detection region of each channel. As a cell passes through the beam pattern of a particular channel, a series of time-spaced peaks will be created in the emitted fluorescence signal. The phase variation lens discussed above can be used to create a holographic effect in this situation. The holographic effect transforms the uniform beam into unique spatial patterns within the detection regions of each channel.

Microfluidic Device Having Transmissive and Reflective Lenses

In prior art systems, the light source is applied to one side of the cytometry device, with the detection optics also only detecting the fluorescence from one side of the sample cell. A transmissive lens or other optic is often used to focus a portion of the emitted photons into the detection optics, however this still limits the amount of photons that are captured from the fluorescent sample cell, since the photons emitted in the opposite direction are not captured by the transmissive lens. The excitation light intensity may be increased to generate more fluorescently generated photons, however this also increases the amount of noise in the signal. Another solution is to use multiple sets of detection optics placed at different locations, although this adds significant expense.

In order to capture as many of the photons generated by a fluorescing sample cell as possible with a single detection optic, a reflective lens may be placed on the side of the sample cell opposite the detection optics. The reflective lens will capture a large portion of the photons not captured by the transmissive lens, reflect them back through the transmissive lens, and into the detection optics. This allows the system to capture more of the emitted photons for a given excitation light intensity without increasing the noise in the received signal, and without the cost of multiple detection optics.

Figure 17:
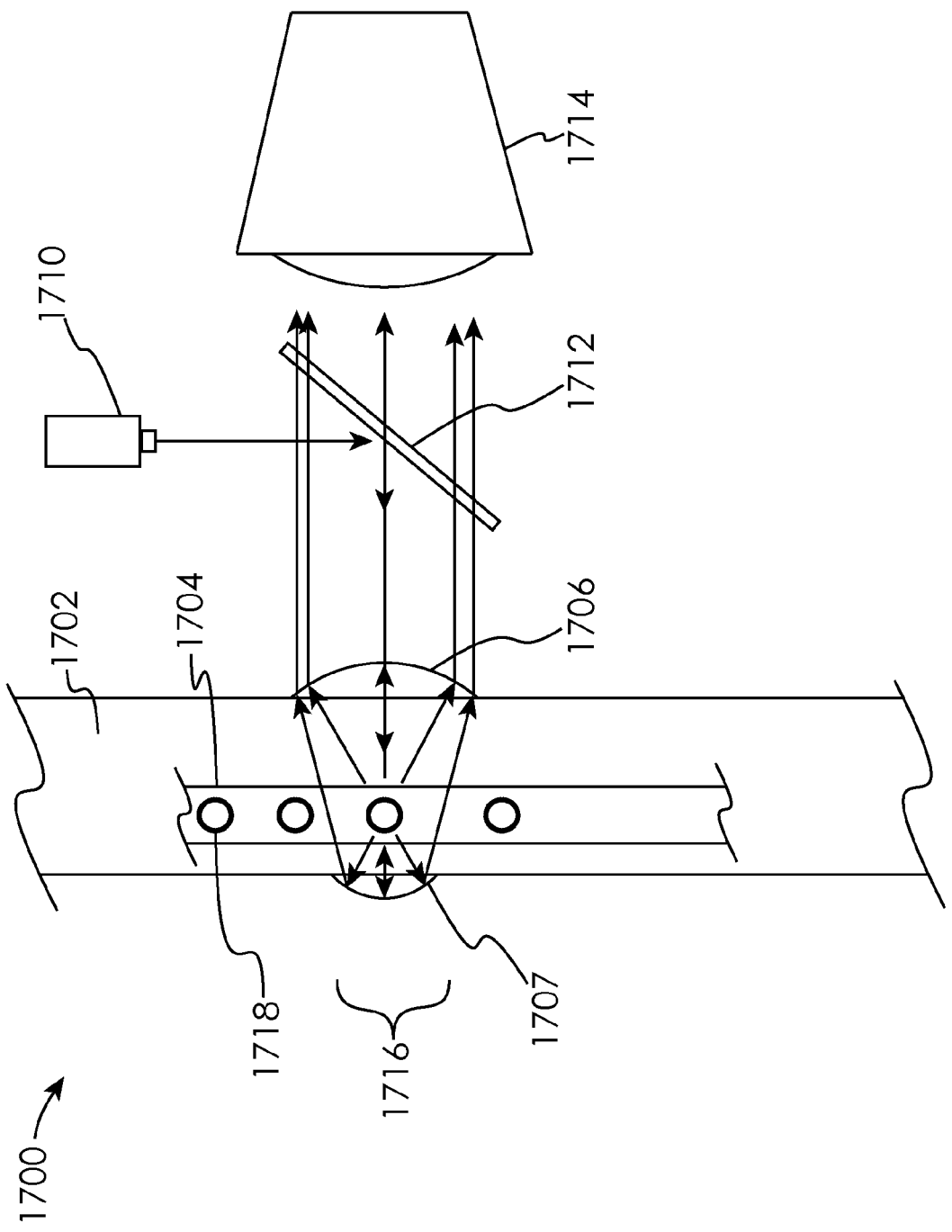
FIG. 17 is a schematic side view of a section of a microfluidic device according to an embodiment of the present disclosure.

FIG. 17 schematically illustrates a system 1700 for analyzing samples using cytometry. The system 1700 may comprise a microfluidic cytometry device formed on substrate 1702 (shown here from a side view) having a detection flow channel 1704 contained therein. For simplicity and ease of illustration, FIG. 17 shows a single channel within the substrate 1702. However, it should be appreciated that the single channel may be representative of multiple cytometry channels and a variety of possible configurations of channels as would occur to one skilled in the art. Various other cytometry components may also be contained on the substrate 1702 but are not critical to the present disclosure.

The system 1700 may further comprise a transmissive lens 1706, reflective lens 1707, excitation light source 1710, dichroic mirror 1712 and detection optics 1714. The transmissive and reflective lenses 1706 and 1707 may be mounted to or formed integrally within the substrate 1702 as illustrated in FIG. 17, or may be placed outside of the substrate 1702 depending the particular application and cost considerations. The excitation light source 1710 may comprise a laser or other light source known in the art. The detection optics 1714 may comprise various light sensing means known in the art, such as photomultiplier tubes.

In operation, excitation light source 1710 directs a light beam towards dichroic mirror 1712. The dichroic mirror is configured to reflect the wavelength received from the excitation light source 1710 to the detection area 1716 within detection channel 1704. When a sample cell 1718 passes through the detection area 1710 and fluoresces, the generated photons are emitted in many directions. Some photons will be emitted back toward the focusing lens 1706, pass through the dichroic mirror 1712 (which is configured to pass the fluorescent wavelength), and sensed by the detection optics 1714. Photons that are emitted from the opposite side of chip 1702 will be captured by reflective lens 1707, directed back to transmissive lens 1706, and be focused into the detection optics 1714.

The relative distance between the transmissive lens 1706, the detection channel 1704, and the reflective lens 1707 is set so that the light reflected from the reflective lens 1707 is also properly focused by the transmissive lens 1706 into the detection optics 1714. For example, the reflective lens 1707 may need to be closer to the detection channel 1704. When the transmissive and reflective lenses 1706 and 1707 are mounted directly on the substrate 1702, this can be accomplished by offsetting the detection channel 1704 as shown in FIG. 17 to ensure proper placement of the transmissive and reflective lenses relative to the detection channel 1704.

Microfluidic Device Having Integrally-Formed Optics

Various optical devices, such as lenses, are often placed in the path of the incoming and/or outgoing light beams in a microfluidic device to provide the maximum photon delivery and recovery to and from the sample cell being observed. Such optical devices are also often needed to change the numerical aperture (NA) of the light emitted from the detection region so that it may be properly received by a fiberoptic cable. This is necessary because the NA of the emitted light is usually very high, while the NA of a fiberoptic cable is usually very low. If the NA of the emitted light is not reduced prior to reaching the fiberoptic cable, only a small portion of the emitted light will be successfully propagated through the fiberoptic cable.

One problem, however, is that the various incoming and outgoing light beams will be subject to refraction as they pass through various materials in the beam path. For example, when a focused excitation beam passes from the air into the substrate of a microfluidic chip (which has a normally flat surface), the beam will refract to some degree, making it more difficult to focus the beam on the intended detection region within the chip. To overcome this problem, the focusing lens or other optic can be formed into the chip substrate itself. Because the air gap between the focusing optic and the chip substrate is eliminated, and because the focusing optic and chip substrate are formed from and remain part of the same piece of material, unwanted refraction of the beam within the chip material is eliminated.

Figure 18:
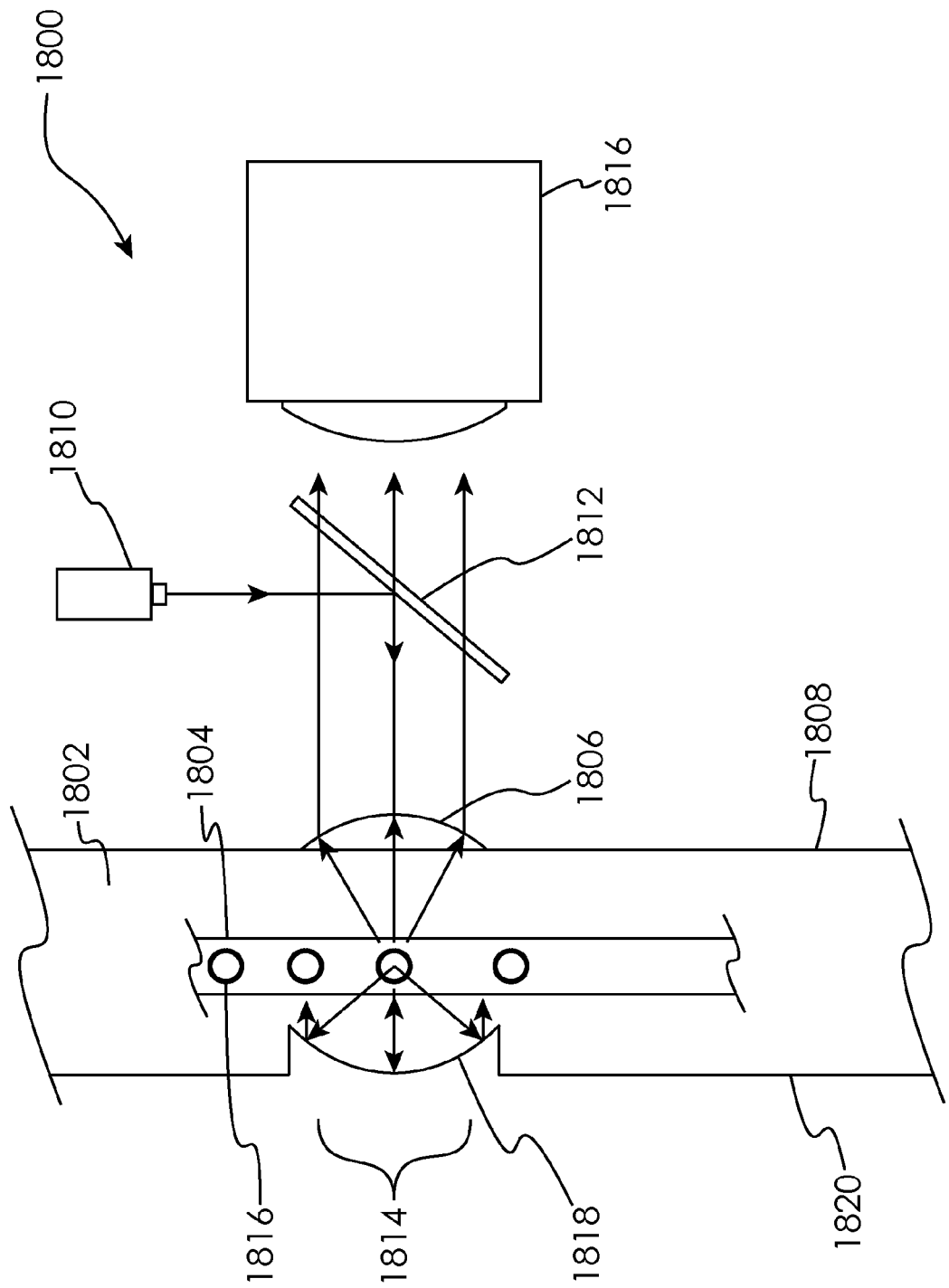
FIG. 18 is a schematic side view of a section of a microfluidic device according to an embodiment of the present disclosure.

FIG. 18 illustrates a system 1800 for analyzing samples using cytometry. The system 1800 may comprise a microfluidic device substrate 1802 (a side view section of which is shown in the figure) having a detection channel 1804 contained therein. For simplicity and ease of illustration, FIG. 18 shows a single channel within the cytometry chip 1802. However, it should be appreciated that the single channel may be representative of multiple cytometry channels and a variety of possible configurations of channels as would occur to one skilled in the art. Various other cytometry components may also be contained on the cytometry chip 1802 as described hereinabove but are not critical to the present disclosure.

The substrate 1802 further comprises an optic 1806, shown here as a focusing lens. The optic 1806 is integrally formed into the substrate of the substrate 1802. This can be accomplished by various methods known in the art. For example, the optic 1806 can be formed into an injection mold which is used to produce the substrate 1802. In other embodiments, the optic 1806 can be machined into or otherwise shaped out of the chip substrate after the basic chip shape is formed.

In operation, excitation light source 1810 directs a light beam towards dichroic mirror 1812. The dichroic mirror 1812 is configured to reflect the wavelength received from the excitation light source 1810 to the detection region 1814 within detection channel 1804. Various other optical components known in the art may be used to direct the excitation light beam to the optic 1806, the details of which are not critical to the present disclosure. When a sample cell 1816 passes through the detection region 1814 and is caused to fluoresce by the excitation light beam, the generated photons will be collected or focused by the optic 1806, pass through the dichroic mirror 1812 (which is configured to pass the fluorescence wavelength), and be finally detected by the detection optics 1816. The detection optics 1816 may comprise various light sensing means known in the art, such as photomultiplier tubes. In certain embodiments, other components known in the art, such as fiber optic cables, may be employed to route the emitted light beams to the detection optics 1816.

It shall be understood that the optic 1806 may comprise any optical element for focusing, spreading, filtering, or otherwise processing the light beams received by or generated from the sample cell 1816 within the detection region 1814. In addition, multiple optical elements may be mounted on the substrate 1802. As one non-limiting example, an additional optic 1818 with a reflective coating may be formed into the opposite surface 1820 of the substrate 1802 to direct additional photons back to the detection optics 1816. In certain applications, it may be advantageous to form the optic 1818 as in intrusion (as opposed to a protrusion) into the surface 1820, as illustrated in FIG. 18. This allows the surface 1820 of the substrate 1802 to be placed flush against a corresponding flat surface within a mounting device (not shown).

Microfluidic Device Having a Non-Integral Geographically Selective Reagent Delivery Structure In many cases, a reagent may need to be added to activate or otherwise prepare the sample before the cytometry analysis is executed. The required reagent may be added to the microfluidic device during manufacturing, eliminating the need for the user to add it at the time of use. However, this requires that many different types of devices will need to be kept in inventory by the manufacturer, with each device adapted for use in only a small number of applications. In order to increase manufacturing efficiency and reduce inventory cost, the reagent may be formed into a separate structure which can be mated with the microfluidic device after manufacturing. This allows the manufacturer to produce a single microfluidic device which can accept a number of different reagent delivery structures.

Figure 19:
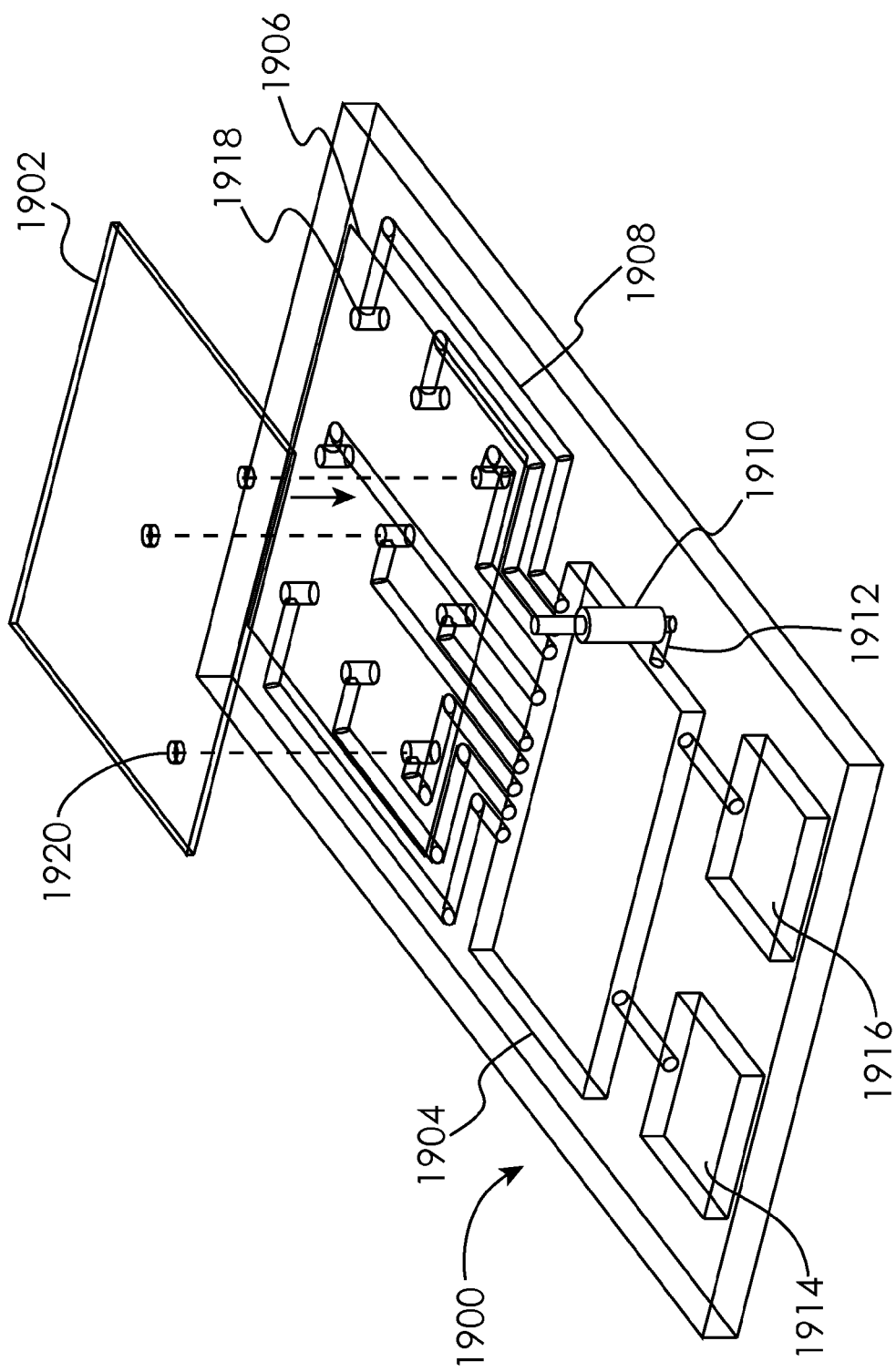
FIG. 19 is a schematic perspective view of a microfluidic device according to an embodiment of the present disclosure.

FIG. 19 illustrates a microfluidic device 1900 which is configured to receive a separate reagent structure 1902. The device 1900 may comprise a cytometry analysis portion 1904 that is connected to a reagent receiving portion 1906 by microfluidic flow channels 1908. The device 1900 also comprises a sample receiving port 1910 for receiving a sample to be analyzed. Sample receiving port 1910 is connected to the cytometry analysis portion 1904 by microfluidic flow channel 1912. In certain embodiments, the reagent delivery structure 1902 is mated to the reagent receiving portion 1906 before a sample is added to the device 1900. This mating can be performed by the user at the time of use or by the manufacturer prior to shipping the device 1900. The cytometry analysis portion 1904 performs cytometry analysis on the received sample and reagent mixture. For example, the cytometry analysis section 1904 may sort desirable cells into an extraction well 1914 and undesirable cells into a waste well 1916. The specific operations that occur in the cytometry analysis section 1904 and the specific routing of the microfluidic channels are not critical to the present disclosure.

The reagent receiving portion 1906 is manufactured with a plurality of receiving wells 1918 arranged in a grid or other standardized layout. Various reagent delivery structures 1902 can then be manufactured which have reagent portions 1920 containing reagents at locations that will correspond to at least one of the receiving wells 1918 when the reagent delivery structure 1902 is mated to the reagent receiving portion 1906. In certain embodiments, the location of specific reagent types within the reagent delivery structure 1902 will also be standardized. For example, any reagent at the location corresponding to a specific receiving well 1918 will always be of the same type. Because of this, the equipment used to apply reagents to the reagent delivery structure 1902 during manufacturing can be optimized to always apply a certain reagent type to the same location, if that reagent is being applied to the particular reagent delivery structure 1902. This also allows the cytometry analysis section 1904 and the various microfluidic flow channels 1908 to be designed and optimized based on a known location of the required reagent.

The reagent delivery structure 1902 may be made of any material known in the art which is suitable for storing reagents. For example, the reagent structure 1902 may be in the form of a tape or other flexible strip, with an adhesive applied to hold the reagent structure 1902 in place once applied to the reagent receiving portion 1906. In certain embodiments, the reagent receiving portion 1906 may be recessed into the device 1900, with reagent delivery structure 1902 being made of a rigid material and sized to fit snugly within the reagent receiving portion 1906, ensuring proper placement of the reagent delivery structure 1902. The receiving wells 1918 may also comprise pins which will pierce the reagent portions 1920 to release or expose the reagents contained within reagent portions 1920 into receiving wells 1918 and channels 1908.

Figure 20:
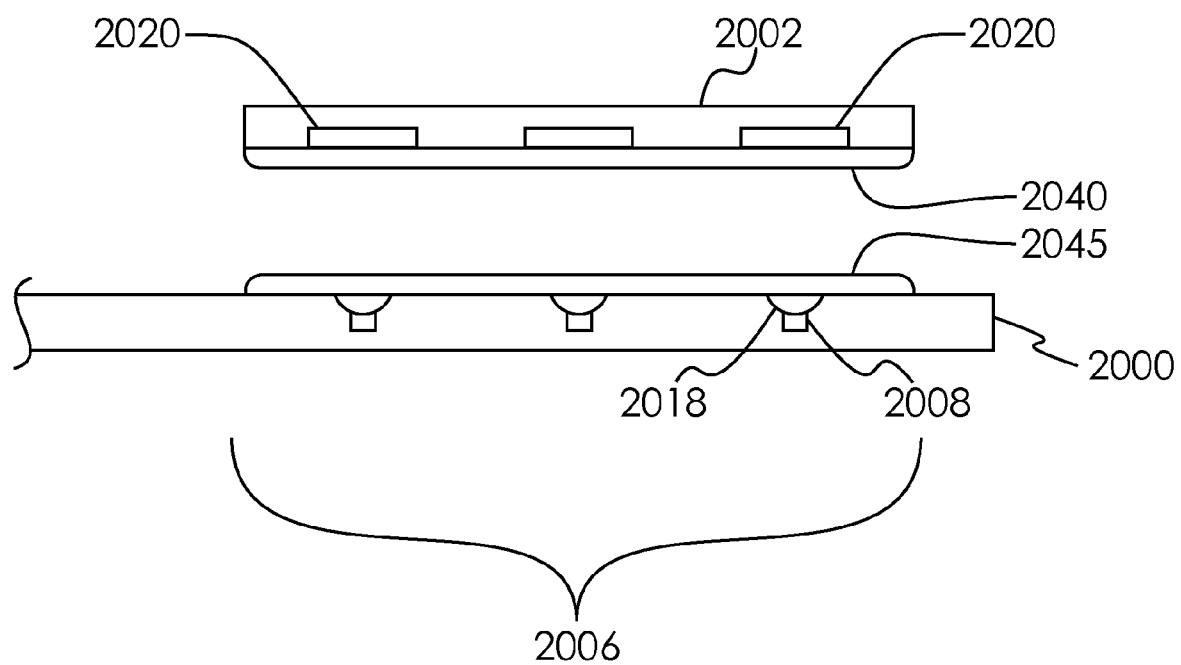
FIG. 20 is a schematic side cross-sectional view of a portion of a microfluidic device according to an embodiment of the present disclosure.

FIG. 20 shows another embodiment where the reagents 2020 contained on reagent structure 2002 are held within the structure 2002 by a soluble barrier 2040. An activation material 2045 is included on the reagent receiving portion 2006 within the device 2000. Once the reagent structure 2002 is applied to the reagent receiving portion 2006, the activation material 2045 will cause the soluble barrier 2040 to dissolve, releasing the reagents 2020 into the reagent receiving wells 2018 and flow channels 2008. In certain embodiments, focused laser beams or acoustic energy applied from an external source may be used to cause the soluble barrier 2040 to dissolve. In still further embodiments, the soluble barrier 2040 and/or the activation material 2045 can be made of a temperature sensitive material, whereby increasing the temperature after mating the reagent structure 2002 to the device 2000 will cause the soluble barrier 2040 to dissolve. Various materials are known in the art which will exhibit this temperature sensitive behavior. For example, the reagents can be provided in agarose, which will preserve the cells contained within the reagent until the agarose is dissolved by heating. In certain embodiments, the soluble barrier 2040 may incorporate micro electrical mechanical structure (MEMS) valves.

Microfluidic Device Incorporating Optical Waveguide in Flow Channel

Certain embodiments of the present disclosure are generally directed to microfluidic devices, such as cytometry chips, having cytometry channels configured as light waveguides to better direct illumination through the channels. In certain embodiments, conforming a cytometry channel into a light waveguide involves choosing materials having desirable indexes of refraction to form the channel walls. Additionally, the effectiveness of the light waveguide channel may also depend on the index of refraction of the fluid passing through the channel. While the waveguide channel according to the present disclosure is discussed herein as directing visible light for sake of brevity, light is just one non-limiting example of numerous possible types of electromagnet radiation which can be directed by the waveguide channel.

Figure 21:
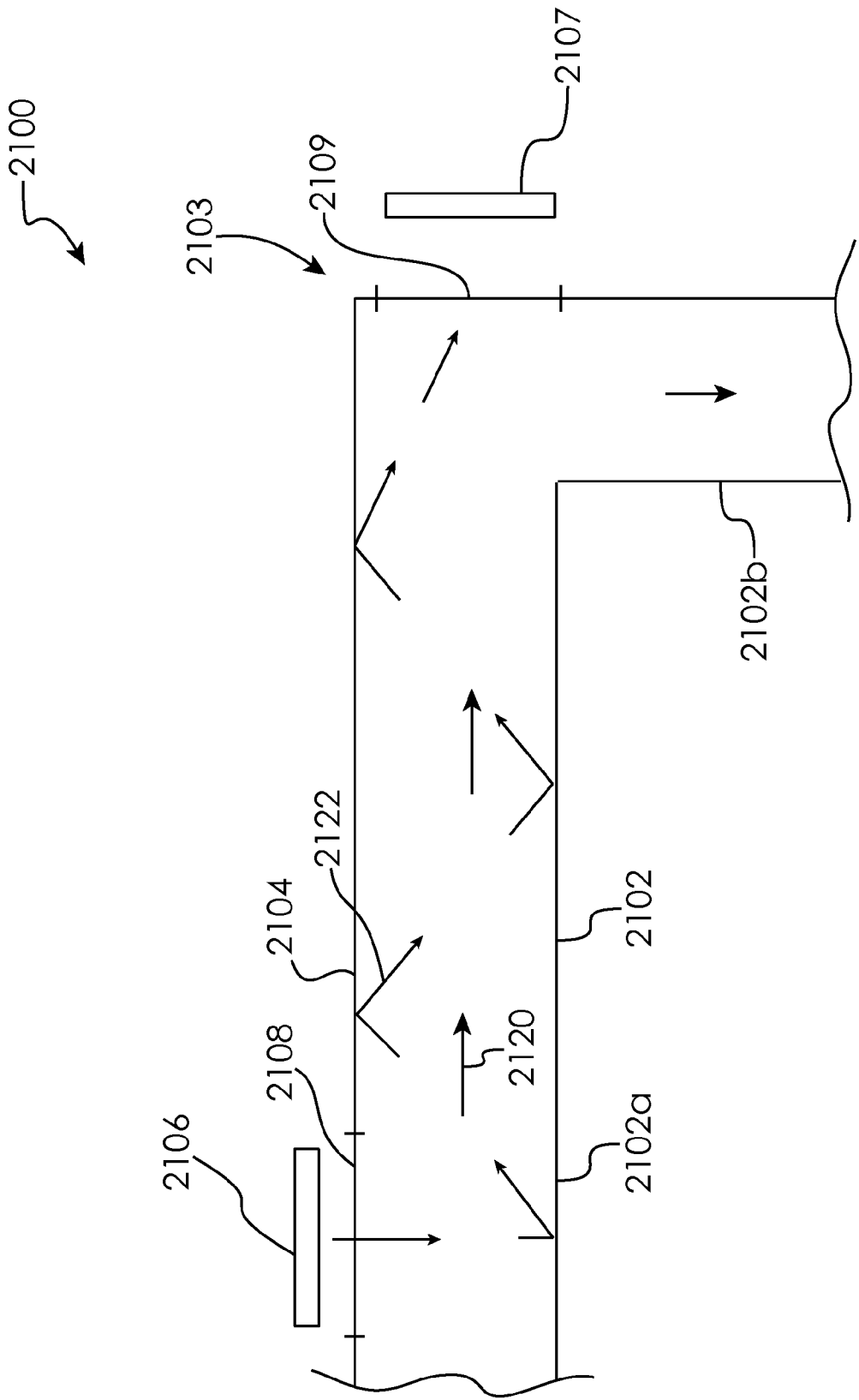
FIG. 21 is a schematic side cross-sectional view of a portion of a microfluidic device according to an embodiment of the present disclosure.

FIG. 21 schematically illustrates a system 2100 having an example cytometry channel 2102 on a microfluidic device as part of a cytometry analysis (such as, for example, flow cytometry or image cytometry) occurring with respect to the device (the specific cytometry analysis operations are not critical to the present disclosure). As illustrated, channel 2102 has a corner 2103 creating two substantially perpendicular sections, 2102a and 2102b. System 2100 includes a light emitting system 2106 and a light collection system 2107 along channel section 2102a, the light being used to illuminate cells for detection as part of the cytometry analysis. In the illustrated example, light collection system 2107 is positioned with its optical axis aligned with the axis of flow through channel section 2102a and light emitting system 2106 is positioned with its optical axis orthogonal to the axis of flow through channel section 2102. It should be appreciated that the specific configurations, positions and operations of systems 2106 and 2107 must correctly couple radiation into the system but are not critical to the present disclosure, the systems being appropriate systems as would occur to one of ordinary skill in the art. The general flow of a biological sample through channel 2102 is illustrated by large-head arrows 2120 within the channel. The light emitted from system 2106 is internally reflected throughout the channel 2102 to collection system 2107 and is generally represented by arrows 2122. As such, channel 2102 may act as a light waveguide.

Channel 2102 receives illumination from light emitting system 2106 and transmits it along the length of channel segment 2102a to be emitted out toward light collection system 2107. To accomplish this, the channel wall 2104 of the channel 2102 may include an appropriate index of refraction along at least segment 2102a to internally reflect the light as it travels through section 2102a. Additionally, the channel wall 2104 may be masked (for example, with a reflective coating) along all or portions of its length of section 2102a so the light is emitted only in desired locations. This arrangement can allow for the channel to only emit light in desired areas, which can be either a continuous or multiple point emission.

In certain embodiments, channel 2102 may include a wall section 2108 aligned with light emitting system 2106 and a wall section 2109 aligned with light collection system 2107 to allow for light emission into and out of the channel. Additionally, in certain embodiments, the wall sections 2108 and 2109 may be constructed of a different material having a different index of refraction from the remainder of wall 2104, the different material and index of refraction being designed to allow for light emission therethrough. As another example, in embodiments in which channel wall 2104 is masked, the wall sections 2108 and 2109 may remain unmasked so that light may pass through.

Figure 22:
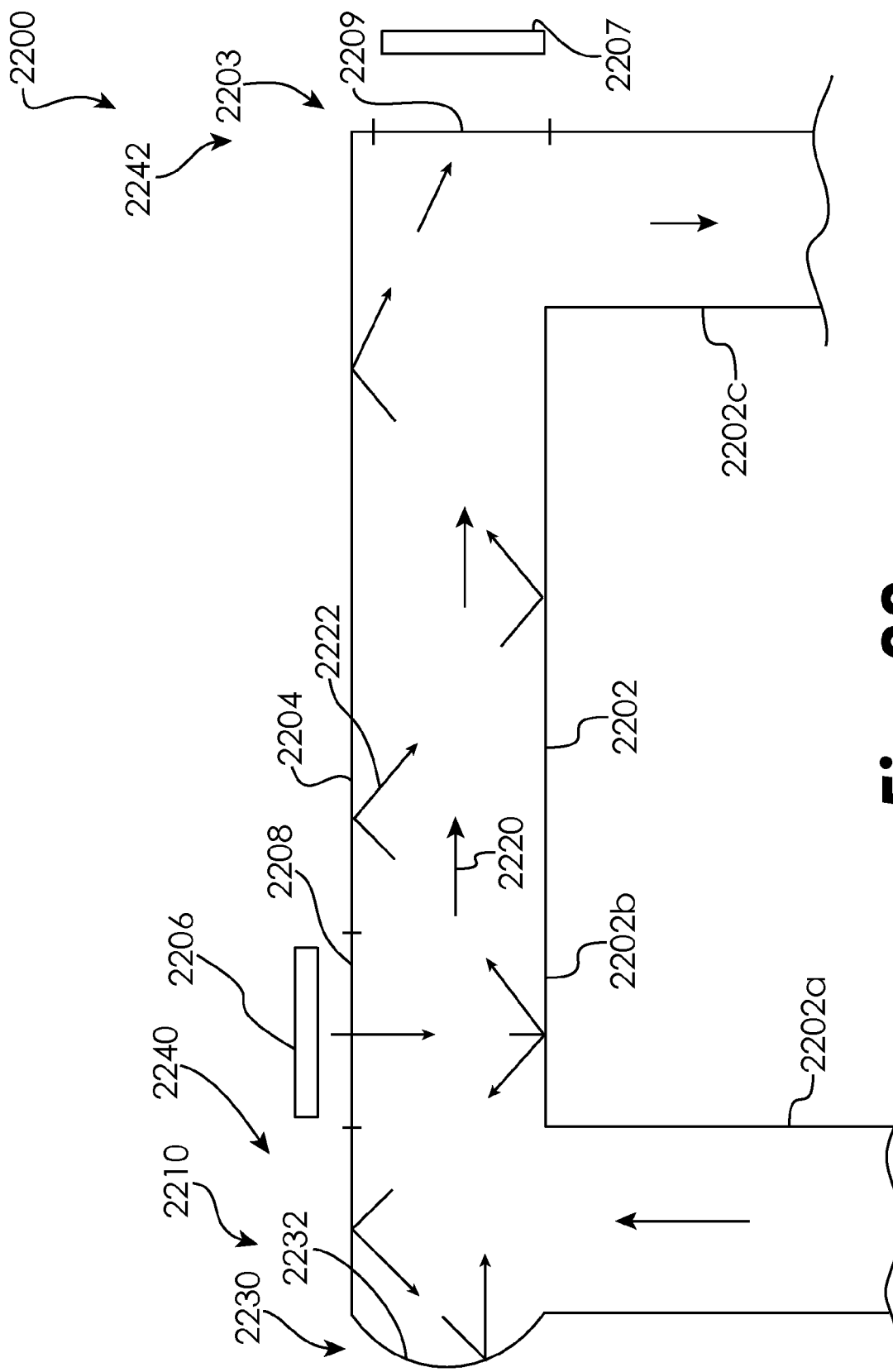
FIG. 22 is a schematic side cross-sectional view of a portion of a microfluidic device according to an embodiment of the present disclosure.

Microfluidic Device Incorporating Optical Waveguide with Reflective Surface in Flow Channel In certain embodiments, a reflective surface can be positioned at one end of the light waveguide channel to further assist in directing the illumination. FIG. 22 schematically illustrates a system 2200 having an example cytometry channel 2202 with a channel wall 2204 on a microfluidic device as part of a cytometry analysis (such as, for example, flow cytometry or image cytometry) occurring with respect to the device (the specific cytometry analysis operations are not critical to the present disclosure). As illustrated, channel 2202 has a corner 2210 between substantially perpendicular channel sections 2220a and 2220b, and a corner 2203 between substantially perpendicular sections 2202b and 2202c. Additionally, channel section 2202b generally includes a first end 2240 adjacent corner 2210 and a second end 2242 adjacent corner 2203. System 2200 includes a light emitting system 2206 and a light collection system 2207 along channel section 2202b, the light being used to illuminate cells for detection as part of the cytometry analysis. In the illustrated example, light collection system 2207 is positioned with its optical axis aligned with the axis of flow through channel section 2202b and light emitting system 2206 is positioned with its optical axis orthogonal to the axis of flow through channel section 2202b. It should be appreciated that the specific configurations, positions and operations of systems 2206 and 2207 must correctly couple radiation into the system but are not critical to the present disclosure, the systems being appropriate systems as would occur to one of ordinary skill in the art.

Additionally, a reflective surface such as mirror 2230 having a mirror surface 2232 is positioned adjacent first end 2240 generally opposite the light collection system 2207. As illustrated, mirror 2230 may be integral with the channel wall 2204. The mirror could be spherical in shape as shown, or it could have other shapes suitable for reflecting emissions coupled from the channel waveguide back down the channel 2202. In other embodiments, the mirror 2230 could be a deformable mirror, generally referred to in the field as an adaptive optic. Such a mirror can have its shape adjusted rapidly under the control of a feedback system.

The general flow of a biological sample through channel 2202 is illustrated by large-head arrows 2220 within the channel. The light emitted from system 2206 is internally reflected throughout the channel 2202 to collection system 2207 and is generally represented by arrows 2222. As such, channel 2202 may act as a light waveguide.

Channel 2202 receives illumination from light emitting system 2206 and transmits it along the length of channel segment 2202b to be emitted out toward light collection system 2207. To accomplish this, the channel wall 2204 of the channel 2202 may include an appropriate index of refraction along at least section 2202b to internally reflect the light as it travels through section 2202b. Additionally, the channel wall 2204 may be masked (for example, with a reflective coating) along all or portions of its length of section 2202b so the light is emitted only in desired locations. This arrangement can allow for the channel to only emit light in desired areas, which can be either a continuous or multiple point emission. Further, spherical mirror surface 2232 is positioned to reflect any portion of the light which may reach mirror 2230 at end 2240 back toward light collection system 2207 at end 2242. The use of the mirror 2230 improves the efficiency and effectiveness of the light waveguide channel by preventing light emitted from system 2206 from being transmitted out end 2240 opposite from system 2207.

In certain embodiments, channel 2202 may include a wall section 2208 aligned with light emitting system 2206 and a wall section 2209 aligned with light collection system 2207 to allow for light emission into and out of the channel. Additionally, in certain embodiments, the wall sections 2208 and 2209 may be configured of a different material having a different index of refraction from the remainder of wall 2204, the different material and index of refraction being designed to allow for light emission therethrough. As another example, in embodiments in which channel wall 2204 is masked, the wall sections 2208 and 2209 may remain unmasked so that light may pass through.

Microfluidic Device for Virus Detection and Sorting

Figure 23:
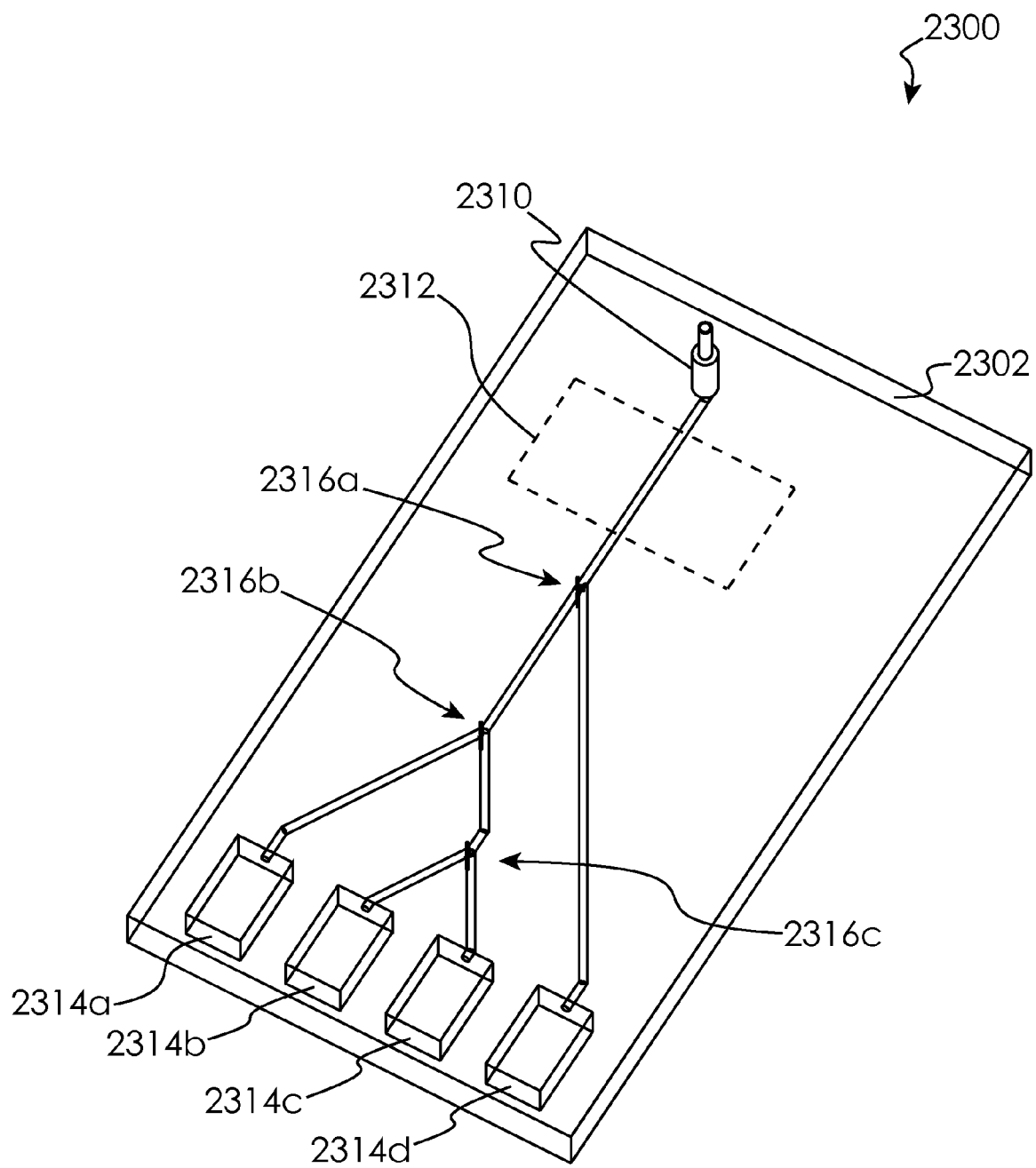
FIG. 23 is a schematic perspective view of a microfluidic device according to an embodiment of the present disclosure.

Certain embodiments of the present disclosure is generally directed to detecting viral particles in a bodily sample by subjecting the sample to a cytometry analysis occurring on a microfluidic device, such as a cytometry chip, and sorting the viral particles into wells or chambers disposed on the chip. The cytometry analysis may be a flow cytometry analysis or an image cytometry analysis. Sorting the viral particles from the bodily sample allows the researcher or medical professional to capture the viral population for further observation or testing. As used herein, the term cytometry is used broadly and meant to include the measurement of any appropriate material, including cells and/or viral particles as two non-limiting examples System 2300, as schematically illustrated in FIG. 23, includes a microfluidic device formed on a substrate 2302 which allows for the detection of viral particles during the cytometry analysis and sorting of the viral particles following the analysis. As part of the system 2300, a bodily sample (not shown) is input to input port 2310 is analyzed via cytometry on substrate 2302 in analysis section 2312 (the specific operations that occur in analysis section 2312 are not critical to the present disclosure). According to the results of the analysis performed, viral particles in the bodily sample input to input port 2310 which were detected in analysis section 2312 may be sorted into one or more chambers 2314. In certain embodiments, the sample wells 2314 have outlet ports (not shown) in fluid communication therewith in order to facilitate removal of the sorted sample from the wells. Sample fluid may be diverted to wells 2314 by appropriate control of flow diverter 2316.

In one embodiment, the flow diverter 2316 is a piezoelectric device that can be actuated with an electric command signal in order to mechanically divert the flow through the flow channel into any of the wells 2314, depending upon the position of the flow diverter 2316. In other embodiments, flow diverter 2316 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

The viral particles may further be sorted into different wells or chambers 2314 based on the intended future use for the particles. For example, viral particles having the same characteristics may be sorted into chamber 2314a where they are fixed for observation by electron microscopy, and sorted into chamber 2314b where they are reacted with chemicals that are under study for their pharmacological efficacy, with the remaining sample being sorted into chambers 2314c and 2314d according to other criteria. In other embodiments, all of the chambers 2314 may receive viral particles detected in analysis section 2312. The chip 2300 may include means for physically diverting the viral particles into the chambers 2314 from the analysis section 2312 as is known in the art. Alternatively, the material in the bodily sample may be used to exit the chip 2300 after the analysis is complete.

In the illustrated embodiment there are four illustrated chambers 2314; however, it should be appreciated that there may be more or less than four chambers as would generally occur to one skilled in the art. The substrate 2302 having a plurality of chambers 2314 may be designed so that a predetermined amount of viral particles is sorted into each chamber. For ease of illustration, the chambers 2314 are illustrated as being horizontally aligned, but it should also be appreciated that the chambers may be positioned otherwise on the chip as would generally occur to one skilled in the art. Additionally, for simplicity and ease of illustration, FIG. 23 shows single channels extending between the components, areas or sections of substrate 2302. However, it should be appreciated that the single channels may be representative of multiple cytometry channels and a variety of possible configurations of channels as would occur to one skilled in the art.

The bodily sample input at input port 2310 may be a blood sample, a urine sample, a tissue sample, a saliva sample, a cell sample, or combinations thereof, just to name a few non-limiting examples. In addition to detecting and sorting the presence of any viral particles in the bodily sample, system 2300 may also be configured to measure the number of viral particles in the sample. In certain embodiments, the cytometry analysis at section 2312 is capable of measuring the number of viral particles in the sample. In other embodiments, the viral particles sorted into the chamber(s) 2314 on the substrate 2302 and can be measured or counted after sorting.

Certain embodiments of the present disclosure are generally directed to detecting (rather than sorting) viral particles in a bodily sample by subjecting the sample to a cytometry analysis occurring on a microfluidic device, such as a cytometry chip. The cytometry analysis may be a flow cytometry analysis or an image cytometry analysis. Using microfluidic device to detect viral particles via cytometry provides increased safety and decreased risk of exposure to the researcher or medical professional due to the controlled nature of the testing on the device. Additionally, the microfluidic device allows the cytometry analysis to be run at a relatively slow rate, allowing for the small viral particles to be detected. Further, the microfluidic device also allows for simultaneous detection of cells and viral particles via one measurement device. As used herein, the term cytometry is used broadly and meant to include the measurement of any appropriate material, including cells and/or viral particles as two non-limiting examples.

In certain embodiments, the viral particles may be labeled with a specific fluorescence probe that recognizes a specific sequence of molecules in the RNA. The cytometry instrument system may detect the presence of the virus particle based on light scattering and classify the particle based on the intensity and wavelength of the fluorescence emission. In some embodiments, multiple fluorescent probes may be used and multiple viruses may be detected in the same biological sample.

In addition to detecting the presence of any viral particles in the bodily sample input at 2310, system 2300 may also be configured to measure the number of viral particles in the sample. In certain embodiments, the cytometry analysis at section 2312 is capable of measuring the number of viral particles in the sample. In other embodiments, the viral particles can be sorted into wells or chambers on the substrate 2302 and can be measured or counted after sorting. In embodiments involving AIDS testing, the number of virus particles per unit of blood in the bodily sample can be measured via the cytometry analysis. Counting the number of virus particles, also referred to the viral load, can be an important measurement in assessing the health of an AIDS patient. If the sample remains on the substrate 2302 after the analysis is performed at section 2312, then the safety of handling the sample is greatly improved, as the entire chip 2300 may be disposed of like any other contaminated medical device (e.g. like a used syringe).

Microfluidic Device Displaying Color Change to Indicate Use or a Result

Certain embodiments of the present disclosure are generally directed to a microfluidic device, such as a cytometry chip, capable of providing a visual indication following a cytometry analysis to indicate the result of the cytometry analysis. The cytometry analysis may be a flow cytometry analysis, as described above, or an image cytometry analysis. In an example embodiment, the visual indication is a color change resulting from dye flooding the components of the device after the analysis is complete if the analysis produced a positive result.

Figure 24:
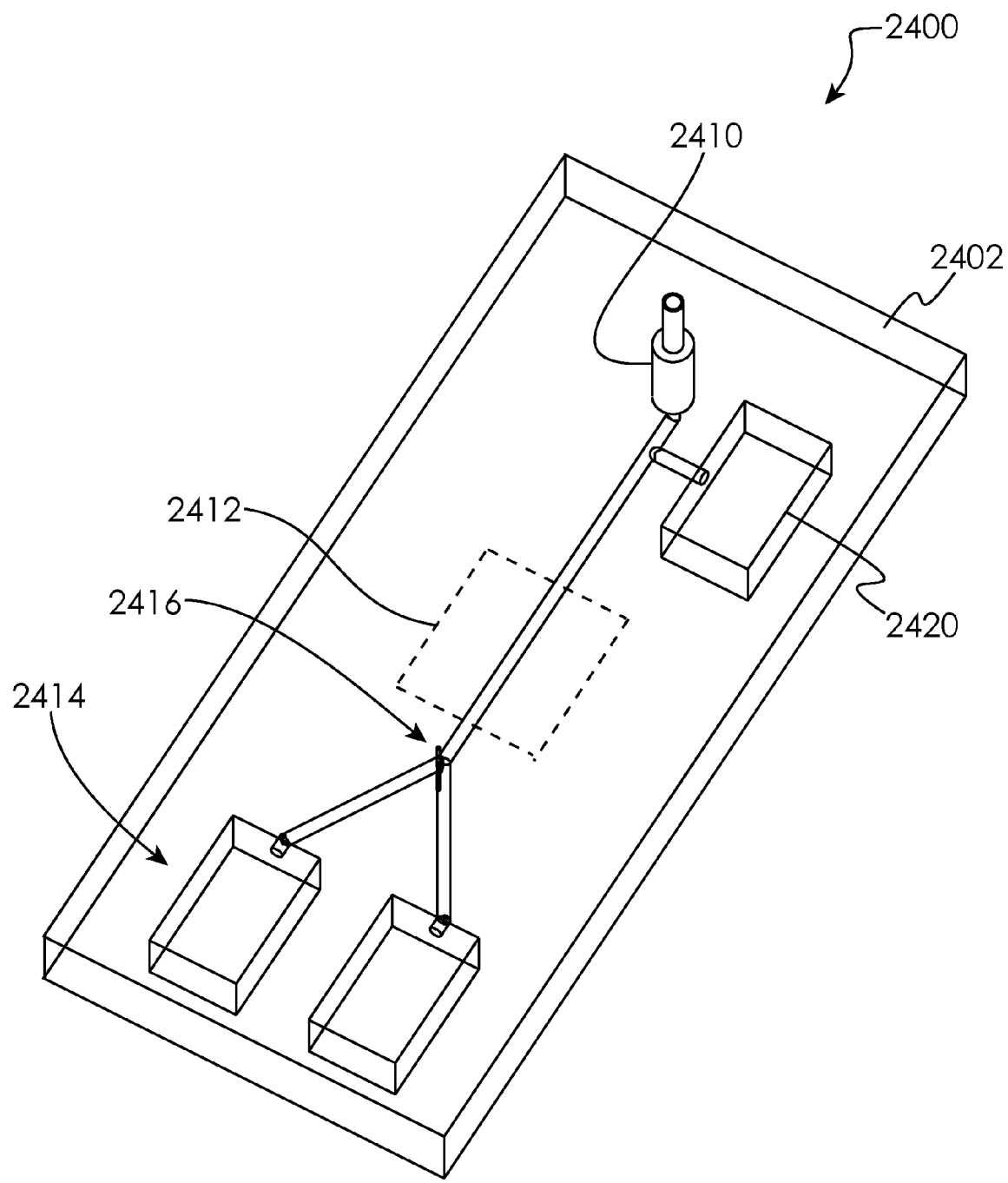
FIG. 24 is a schematic perspective view of a microfluidic device according to an embodiment of the present disclosure.

FIG. 24 illustrates a system 2400 in which cells from a cell supply (not shown) are input to input port 2410 on substrate 2402 and are analyzed via cytometry in analysis section 2412 (the specific operations that occur in analysis section 2412 are not critical to the present disclosure). According to the results of the analysis performed, the cells may optionally be sorted into different chambers 2414 based on differing characteristics of the cells. In certain embodiments, the sample wells 2414 have outlet ports (not shown) in fluid communication therewith in order to facilitate removal of the sorted sample from the wells. Sample fluid may be diverted to wells 2414 by appropriate control of flow diverter 2416.

In one embodiment, the flow diverter 2416 is a piezoelectric device that can be actuated with an electric command signal in order to mechanically divert the flow through the flow channel into either of the wells 2414, depending upon the position of the flow diverter 2416. In other embodiments, flow diverter 2416 is not a piezoelectric device, but instead can be, for example, an air bubble inserted from the wall to deflect the flow, a fluid deflector moved or actuated by a magnetic field or any other flow diverter or sorting gate as would occur to one of ordinary skill in the art.

Cells may be sorted into different wells or chambers 2414 based on the intended future use for the cells. For example, cells having the same characteristics, or phenotype, may be sorted into one well where they are fixed for viewing, and sorted into another well where they are maintained in a viable state to undergo additional functional measurements. Alternatively, the cells may be deposited into the wells or chambers 2414 based on volume as opposed to a sorting method. The chip may include means for physically diverting the cells into the chambers 2414 from the analysis section 2412 as is known in the art. Alternatively, the cells may be caused to exit the substrate 2402 after the analysis is complete. For simplicity and ease of illustration, FIG. 24 shows single channels extending between the components, areas or sections of substrate 2402. However, it should be appreciated that the single channels may be representative of multiple cytometry channels and a variety of possible configurations of channels as would occur to one skilled in the art.

In the particular embodiment illustrated in FIG. 2, a dye may be contained in a dye repository 2420 and stored for later use on the device. After the cells are analyzed and optionally sorted, and if the analysis produced a positive result as defined by some predetermined criteria, the dye may be allowed to flow out of repository 2420 and travel through the components of chip 2402 to provide a visual indication of the positive result via the color of the dye. In the particular illustrated embodiment, the dye may be released from repository 2420, flow to and through the sample channel 2409, flow through analysis section 2412, and flow into optional chambers 2414. In other embodiments, the dye may flow from repository 2420 (which may be opaque such that the dye therein is not visible) to a second non-opaque repository (not shown) in which the dye is visible external to the chip 2400. However, it should be appreciated that the flow of the dye may occur in many different configurations or arrangements as would occur to one skilled in the art. To that end, the dye repository 2420 is shown as being positioned near the top of the chip; however, it should be appreciated that the repository may be positioned elsewhere on the chip. The dye contained within repository 2420 and used to provide the visual indication may be any appropriate colored dye as would occur to one skilled in the art. In other embodiments, the material contained in the repository and used to provide the visual indication is another appropriate colored material as would occur to one of ordinary skill in the art. In still other embodiments, more than one dye repository is provided, such that the color change is produced by mixing the contents of both repositories to produce a color change when mixed. The materials in the repositories may be two fluids, a fluid and a non-fluid, or two non-fluids.

Release of the dye from repository 2420 may be accomplished by manual operation by a user of the chip 2402. Alternatively, release of the dye may be accomplished under control of the device or instrument system performing the cytometry analysis 2412, such as by opening a valve maintaining the dye within the repository 2420, as is known in the art. The repository 2420 may take any convenient physical form, such as a well formed into the surface of substrate 2402, which may remain open or may include a cover that is glued in placed, snapped in place with resilient members that engage the substrate 2402, slide in place under guides that extend from the substrate 2402 surface, or any other convenient means as would occur to one of ordinary skill in the art.

The above examples are intended to be only non-limiting examples of many possible configurations.

Additionally, other manners of providing a visual indication of a result of the cytometry analysis as would occur to one of ordinary skill in the art are contemplated by the present disclosure, with the release of a dye being just one non-limiting example of numerous possible mechanisms. As an alternative example, the chip 2400 may include sensors incorporated therewith which are operable to provide a visual indication of a result of the cytometry analysis. As another alternative example, the visual indication can be done by providing a mechanism which immerses the chip 2400 in a colored or dye solution and allowing the solution to spread through the components of the chip. In another alternative example, a section of the substrate 2402 is coated with a light-sensitive material and may change in color due to a chemical reaction caused by electromagnetic stimulation. As another alternative example, the dye may be deposited on the chip 2400 in a dried form and hydrated by sheath fluid diverted to the appropriate location. The chip 2400 may be configured to provide a visual indication on the occurrence of a positive result of the cytometry analysis or alternatively may be configured to provide different visual indications corresponding to the different possible results of the analysis.

In embodiments in which the cytometry analysis is being run to determine if cells, tissue or other material include a dangerous or hazardous component, such as in AIDS or Hepatitis testing as examples, providing a visual indication of a positive result will provide an indication to the researcher or medical professional that the chip 2400 includes a dangerous or hazardous pathogen. In this way, the researcher or medical professional can sterilize, dispose of or otherwise handle the chip 2400 as necessary. Combined with the sterilization, the color change may function to indicate that the chip 2400 has been successfully decontaminated. Additionally, in many cytometry analysis environments, the researcher or medical professional may desire to run one or more additional cytometry analyses on a cell sample following a positive result to verify the accuracy of the result. The visual indication of a positive result allows the researcher or medical professional to immediately run additional testing if desired.

In other embodiments, the chip 2400 may be configured to simply provide a visual indication that the chip has been used. For example, providing a clear indication that the chip 2400 has been used may prevent accidental contamination of cell samples that could occur if a second cell sample were run through a used chip 2400. Other manners of providing a visual indication that the microfluidic device has been used as would occur to one of ordinary skill in the art are contemplated by the present disclosure. As another example, the analysis section 2412 and/or chambers 2414 may include sensors coupled therewith which provide a visual indication that either the analysis in section 2412 is complete or the cells have been collected into the chambers 2414, respectively. The sensors may themselves provide a visual indication via color change, or may direct the visual indication on the chip 2400. In even a further example, a waste chamber or channel on the chip 2400 may be pre-coated with a chemical or dye that changes color when it comes in contact with fluid. In this way, any chip that has had fluid flow in it would be identified as used via the color change.

Additionally, in certain embodiments the chip 2400 may be designed to provide a visual indication when one or more steps throughout the cytometry analysis process have been completed. As an example, one or more of the cell sample input 2410, analysis section 2412 and chambers 2414 may include mechanisms to provide a visual indication that the particular step associated with that component has been completed. Accordingly, a researcher or medical professional viewing the chip 2400 may easily determine the present status of the cytometry analysis, such as the cell sample has been loaded, the cytometry analysis is complete, or the cells have been sorted. The mechanisms to provide a visual indication at the particular stages of the cytometry analysis may be any appropriate mechanism for providing a visual indication as would occur to one skilled in the art.

With all of the embodiments disclosed herein, the use of a microfluidic device on a substrate offers many advantages, one of which is that the microfluidic device may be treated as a disposable part, allowing a new microfluidic device to be used for sorting each new sample of cells. This greatly simplifies the handling of the sorting equipment and reduces the complexity of cleaning the equipment to prevent cross contamination between sorting sessions, because much of the hardware through which the samples flow is simply disposed of. The microfluidic device also lends itself well to sterilization (such as by gamma irradiation) before being disposed of.

While the disclosure has been illustrated and described in detail in the drawings and foregoing description, the same is to be considered as illustrative and not restrictive in character, it being understood that only the preferred embodiments have been shown and described and that all changes and modifications that come within the spirit of the disclosure are desired to be protected.

What is claimed:

1. A method of detecting particles in a sample, the method comprising the steps of:
   a) providing a microfluidic device, said microfluidic device comprising:
   a substrate;
   a first microfluidic flow channel formed in said substrate, wherein said first flow channel extends through a portion of said substrate adapted to facilitate cytometry analysis of first cells flowing in said first flow channel; and
   a second microfluidic flow channel formed in said substrate, wherein said second flow channel extends through a portion of said substrate adapted to facilitate cytometry analysis of second cells flowing in said second flow channel;
   b) producing an excitation beam aimed at said first and second flow channels;
   c) spatially varying said excitation beam in a first patterned manner prior to said excitation beam reaching said first flow channel such that a first patterned excitation beam illuminates said first flow channel; and
   d) spatially varying said excitation beam in a second patterned manner prior to said excitation beam reaching said second flow channel such that a second patterned excitation beam illuminates said second flow channel.

2. A method of detecting particles in a sample, the method comprising the steps of:
   a) providing a microfluidic device, said microfludic device comprising:
   a substrate;
   a microfluidic flow channel formed in said substrate, wherein said flow channel extends through a portion of said substrate adapted to facilitate cytometry analysis of cells flowing in said flow channel;
   a sample reception well formed onboard said substrate, said sample reception well being fluidically coupled to said flow channel; and
   an electromagnet disposed onboard said substrate and operative when energized to produce a magnetic field within said sample reception well;
   b) labeling a first portion of said particles with labels that respond to said magnetic field, thereby creating labeled particles and non-labeled particles;
   c) labeling a second portion of said particles with labels that fluoresce when excited by an appropriate radiation source, wherein said second portion is less than all of said particles;
   d) introducing said particles into said sample reception well such that said labeled first portion of particles are moved by said magnetic field;
   e) causing at least a portion of particles, selected from the group consisting of: said labeled particles and said non-labeled particles, to enter said flow channel; and
   f) performing flow cytometry analysis on said portion of particles in said flow channel.

3. A microfluidic device, comprising:
   a substrate having a top surface and a bottom surface;
   a microfluidic flow channel formed in said substrate, wherein said flow channel extends through a portion of said substrate adapted to facilitate through said top surface cytometry analysis of cells flowing in said flow channel; and
   at least one leg positioned on said bottom surface of said substrate, said at least one leg facilitating stacking said microfluidic device on another microfluidic device.

* * * * *